United States Patent
Hazlett et al.

(10) Patent No.: US 11,666,647 B2
(45) Date of Patent: Jun. 6, 2023

(54) AUTOTRANSPORTER-MEDIATED DISPLAY OF COMPLEMENT RECEPTOR LIGANDS BY BACTERIAL IMMUNOGENS

(71) Applicant: ALBANY MEDICAL COLLEGE, Albany, NY (US)

(72) Inventors: Karsten Hazlett, East Berne, NY (US); Kristen M. Tummillo, Union, NJ (US); Edmund J. Gosselin, Delanson, NY (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 232 days.

(21) Appl. No.: 17/036,526

(22) Filed: Sep. 29, 2020

(65) Prior Publication Data

US 2022/0096618 A1 Mar. 31, 2022

(51) Int. Cl.
*A61K 39/02* (2006.01)
*C12N 15/87* (2006.01)
*A61K 38/17* (2006.01)
*A61K 38/16* (2006.01)
*A61K 39/00* (2006.01)

(52) U.S. Cl.
CPC ............ *A61K 39/02* (2013.01); *A61K 38/164* (2013.01); *A61K 38/1725* (2013.01); *C12N 15/87* (2013.01); *A61K 2039/55516* (2013.01); *C12N 2310/3517* (2013.01); *C12N 2800/10* (2013.01)

(58) Field of Classification Search
CPC .. A61K 39/02; A61K 38/164; A61K 38/1725; A61K 2039/523; C12N 15/87; C12N 2310/3517; C12N 2800/10; C07K 2319/02; C07K 2319/43; C07K 14/24; C07K 14/255; C07K 14/472; A61P 31/04
See application file for complete search history.

(56) References Cited

PUBLICATIONS

Pompa-Mera, et al. (2014). Protective immunity against enteral stages of Trichinella spiralis elicited in mice by live attenuated Salmonella vaccine that secretes a 30-mer parasite epitope fused to the molecular adjuvant (Year: 2014).*

Cotter, S. E., Surana, N. K., & Geme III, J. W. S. (2005). Trimeric autotransporters: a distinct subfamily of autotransporter proteins. Trends in microbiology, 13(5), 199-205. (Year: 2005).*

Johnson, S. L., Daligault, H. E., Davenport, K. W., Jaissle, J., Frey, K. G., Ladner, J. T., . . . & Chain, P. S. (2015). Thirty-two complete genome assemblies of nine *Yersinia species*, including *Y. pestis, Y. pseudotuberculosis*, and *Y. enterocolitica*. Genome announcements, 3(2), e00148-15. (Year: 2015).*

Oberhettinger, P., Schutz, M., Raddatz, G., Keller, H., Autenrieth, I. B., & Linke, D. (2011). The sequence of the pYV virulence plasmid from Yersinia enterocolitica strain WA-314 biogroup 1B serotype O: 8. Plasmid, 65(1), 20-24. (Year: 2011).*

Foultier, B., & Cornelis, G. R. (2003). DNA sequence and analysis of the pYVa127/90 virulence plasmid of Yersinia enterocolitica strain A127/90. Research in microbiology, 154(8), 553-557. (Year: 2003).*

Fey, (1984). Nucleotide sequence of complementary DNA and derived amino acid sequence of murine complement protein C3. Philosophical Transactions of the Royal Society of London. B, Biological Sciences, 306(1129), 333-344 (Year: 1984).*

Mammalian Gene Collection (MGC) Program Team. (2002). Generation and initial analysis of more than 15,000 full-length human and mouse cDNA sequences. Proceedings of the National Academy of Sciences, 99(26), 16899-16903. (Year: 2002).*

Wiebauer, K., Domdey, H., Diggelmann, H., & Fey, G. (1982). Isolation and analysis of genomic DNA clones encoding the third component of mouse complement. Proceedings of the National Academy of Sciences, 79(23), 7077-7081. (Year: 1982).*

* cited by examiner

*Primary Examiner* — Louise W Humphrey
*Assistant Examiner* — Kimberly Breen
(74) *Attorney, Agent, or Firm* — David Nocilly

(57) ABSTRACT

An approach for modifying multiple types of bacteria to produce surface modifications that enhance the immunologic response when used as a vaccine. A series of plasmids (pYF, pYFC, pYFP, pSF, pSPF, and pSCF) may be used to transform bacteria which then produce surface-exposed ligands that bind to complement receptors on antigen presenting cells. When modified bacteria are used as a vaccine, the vaccine recipients produce significantly higher titers of specific antibodies and are better protected against challenges from the disease-causing bacteria.

13 Claims, 20 Drawing Sheets

Figure 1:
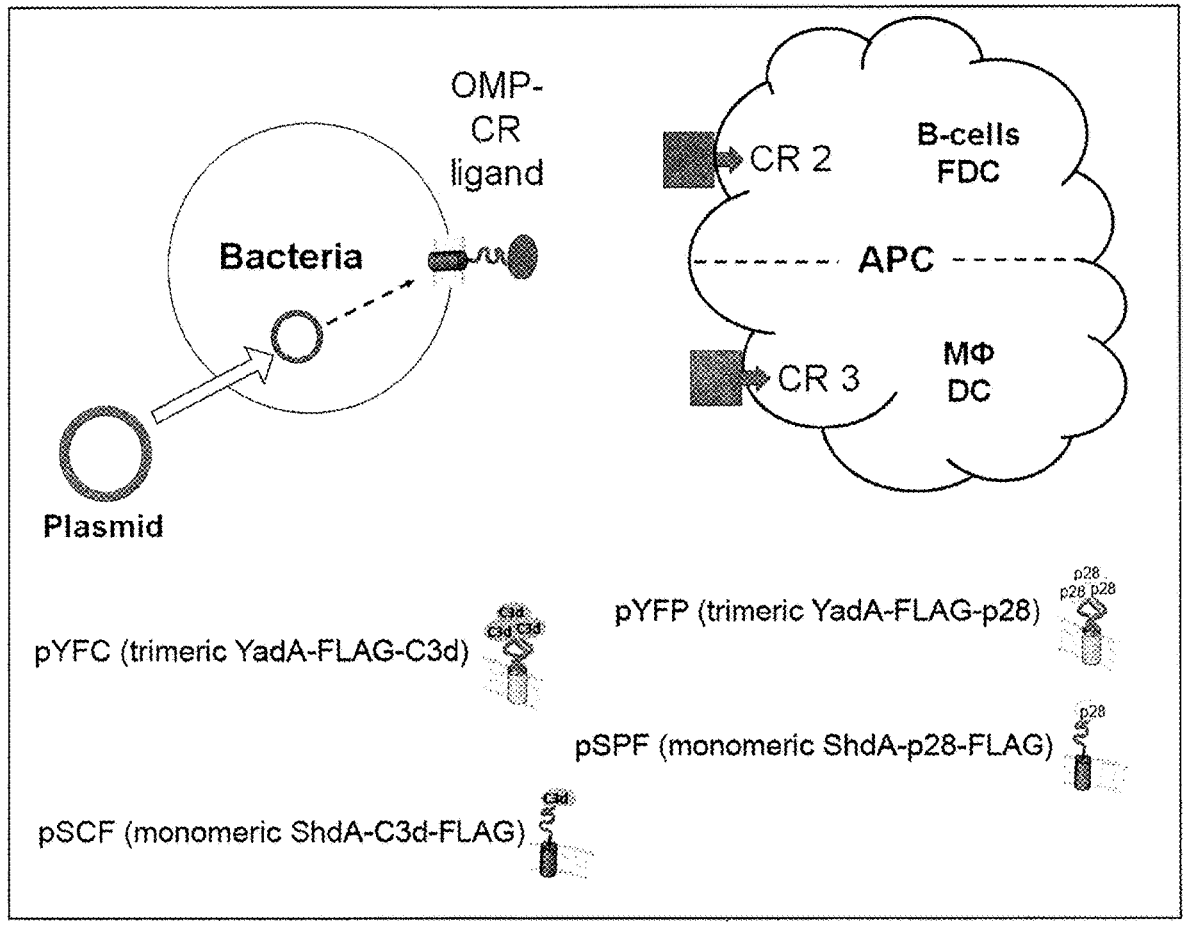

Specification includes a Sequence Listing.

FIG. 6 aggaaacagctatgaccatgattacgccaagcttggtacttgtatggattagtcgagctaaaaagctcatattttttatattcaa
actatataccccttcaagctttgaaaaataaacttaattattatatatgttatttagctagttttttttaattaaagttaaaatcgagagc
ttgtttgacaaaaaaacaaaaaaatttcttgaaaatttttttttttgactcaatatctagacttgcaagagcttggaactttgagatt
gttctaagatgcatacaaattcaaaatgcttaaacaaaaataatttaacaaaggagtaagattgttatgaacattcgtccatt
acaagatagagtattagttcgtcgtgca ggt acc atat gaa ttc act aaa gaa ata taa aag gtg ctt aca
ATG ACT AAA GAT TTT AAG ATC AGT GTC TCT GCG GCA TTA ATA TCT GCG
TTG TTC TCA TCT CCA TAT GCA TTT GCC AAT AAT GAC GAG CTC GAC TAT
AAG GAC GAT GAT GAC AAA TTG GAT ATG GCA AAA AAA CAC TCA AAT AGT
GTT GCT AGA ACA ACT TTA GAA ACT GCT GAA GAA CAT ACA AAT AAA AAA
TCA GCT GAG ACG TTA GCA AGC GCT AAT GTG TAT GCA GAC AGC AAG TCT
TCT CAC ACA CTA AAA ACT GCA AAT AGC TAT ACC GAT GTG ACC GTA AGT
AAT TCG ACT AAG AAA GCA ATC CGT GAA TCG AAT CAA TAC ACA GAT CAT
AAA TTC CAT CAA CTT GAC AAC CGT TTA GAT AAA CTT GAC ACA CGA GTT
GAC AAA GGT TTA GCC AGT TCA GCC GCT TTA AAC AGC TTG TTC CAG CCA
TAT GGT GTG GGG AAA GTA AAC TTT ACT GCA GGT GTC GGG GGA TAT CGC
TCT AGT CAG GCA TTA GCA ATT GGT TCT GGC TAT CGT GTA AAT GAG AGT
GTC GCA CTT AAA GCC GGT GTG GCT TAT GCC GGT TCC TCG GAT GTC ATG
TAC AAT GCA TCA TTT AAT ATC GAG TGG taa tag gttt atc
ggaccgttccaacttaccgaccagttcggcaggtatg (SEQ ID NO: 1)

FIG. 10 aggaaacagctatgaccatgattacgccaagcttggtacttgtatggattagtcgagctaaaaagctcatatttttatattcaa
actatataccccttcaagctttgaaaaataaacttaattattatatatgttatttagctagtttttttaattaaagttaaaatcgagagc
ttgtttgacaaaaaaacaaaaaaatttcttgaaaattttttttttgactcaatatctagacttgcaagagcttggaactttgagatt
gttctaagatgcatacaaattcaaaatgcttaaacaaaaataatttaacaaaggagtaagattgttatgaacattcgtccatt
acaagatagagtattagttcgtcgtgca ggt acc atat gaa ttc act aaa gaa ata taa aag gtg ctt aca
ATG ACT AAA GAT TTT AAG ATC AGT GTC TCT GCG GCA TTA ATA TCT GCG
TTG TTC TCA TCT CCA TAT GCA TTT GCC AAT AAT GAC GAG CTC GGG GGG
GAA CAG AAC ATG ATT GGC ATG ACA CCA ACA GTC ATT GCG GTA CAC TAC
CTG GAC CAG ACC GAA CAG TGG GAG AAG TTC GGC ATA GAG AAG AGG CAA
GAG GCC CTG GAG CTG ATC AAG AAA GGG TAC ACC AGC AGC TG GCC TTC
AAA CAG CCC AGC TCT GCC TAT GCT GCC TTC AAC AAC CGG CCC CCC AGC
ACC TGG CTG ACA GCC TAC GTG GTC AAG GTC TTC TCT CTA GCT GCC AAC
CTC ATC GCC ATC GAC TCT CAC GTC CTG TGT GGG GCT GTT AAA TGG TTG
ATT CTG GAG AAA CAG AAG CCG GAT GGT GTC TTT CAG GAG GAT GGG CCC
GTG ATT CAC CAA GAA ATG ATT GGT GGC TTC CGG AAC GCC AAG GAG GCA
GAT GTG TCA CTC ACA GCC TTC GTC CTC ATC GCA CTG CAG GAA GCC AGG
GAC ATC TGT GAG GGG CAG GTC AAT AGC CTT CCT GGG AGC ATC AAC AAG
GCA GGG GAG TAT ATT GAA GCC AGT TAC ATG AAC CTG CAG AGA CCA TAC
ACA GTG GCC ATT GCT GGG TAT GCC CTG GCC CTG ATG AAC AAA CTG GAG
GAA CCT TAC CTC GGC AAG TTT CTG AAC ACA GCC AAA GAT CGG AAC CGC
TGG GAG GAG CCT GAC CAG CAG CTC TAC AAC GTA GAG GCC ACA TCC TAC
GCC CTC CTG GCC CTG CTG CTG CTG AAA GAC TTT GAC TCT GTG CCC CCT
GTA GTG CGC TGG CTC AAT GAG CAA AGA TAC TAC GGA GGC GGC TAT GGC
TCC ACC CAG GCT ACC TTC ATG GTA TTC CAA GCC TTG GCC CAA TAT CAA
ACA GAT GTC CCT GAC CAT AAG GAC TTG AAC GGA GGT GAG CTC GAC TAT
AAG GAC GAT GAT GAC AAA TTG GAT ATG GCA AAA AAA CAC TCA AAT AGT
GTT GCT AGA ACA ACT TTA GAA ACT GCT GAA GAA CAT ACA AAT AAA AAA
TCA GCT GAG ACG TTA GCA AGC GCT AAT GTG TAT GCA GAC AGC AAG TCT
TCT CAC ACA CTA AAA ACT GCA AAT AGC TAT ACC GAT GTG ACC GTA AGT
AAT TCG ACT AAG AAA GCA ATC CGT GAA TCG AAT CAA TAC ACA GAT CAT
AAA TTC CAT CAA CTT GAC AAC CGT TTA GAT AAA CTT GAC ACA CGA TTT
GAC AAA GGT TTA GCC AGT TCA GCC GCT TTA AAC AGC TTG TTC CAG CCA
TAT GGT GTG GGG AAA GTA AAC TTT ACT GCA GGT GTC GGG GGA TAT CGC
TCT AGT CAG GCA TTA GCA ATT GGT TCT GGC TAT CGT GTA AAT GAG AGT
GTC GCA CTT AAA GCC GGT GTG GCT TAT GCC GGT TCC TCG ATG TC ATG
TAC AAT GCA TCA TTT AAT ATC GAG TGG taa tag gttt atc
ggaccgttccaacttaccgaccagttcggcaggtatg (SEQ ID NO: 2)

FIG. 11 aggaaacagctatgaccatgattacgccaagcttggtacttgtatggattagtcgagctaaaaagctcatattttttatattcaa
actatatacccttcaagctttgaaaaataaacttaattattatatatgttatttagctagttttttttaattaaagttaaaatcgagagc
ttgtttgacaaaaaaacaaaaaaatttcttgaaaattttttttttgactcaatatctagacttgcaagagcttggaactttgagatt
gttctaagatgcatacaaattcaaaatgcttaaacaaaaataatttaacaaaggagtaagattgttatgaacattcgtccatt
acaagatagagtattagttcgtcgtgca ggt acc atat gaa ttc act aaa gaa ata taa aag gtg ctt aca
ATG ACT AAA GAT TTT AAG ATC AGT GTC TCT GCG GCA TTA ATA TCT GCG
TTG TTC TCA TCT CCA TAT GCA TTT GCC AAT AAT GAC GAG CTC AAG TTT CTG
AAC ACA GCC AAA GAT CGG AAC CGC TGG GAG GAG CCT GAC CAG CAG CTC
TAC AAC GTA GAG GCC ACA TCC TAC GCC GGG GGA GGT GGG AGC AGC GGA
GGA GGT GGC AGC AGC GAG CTC GAC TAT AAG GAC GAT GAT GAC AAA TTG
GAT ATG GCA AAA AAA CAC TCA AAT AGT GTT GCT AGA ACA ACT TTA GAA
ACT GCT GAA GAA CAT ACA AAT AAA AAA TCA GCT GAG ACG TTA GCA AGC
GCT AAT GTG TAT GCA GAC AGC AAG TCT TCT CAC ACA CTA AAA ACT GCA
AAT AGC TAT ACC GAT GTG ACC GTA AGT AAT TCG ACT AAG AAA GCA ATC
CGT GAA TCG AAT CAA TAC ACA GAT CAT AAA TTC CAT CAA CTT GAC AAC
CGT TTA GAT AAA CTT GAC ACA CGA GTT GAC AAA GGT TTA GCC AGT TCA
GCC GCT TTA AAC AGC TTG TTC CAG CCA TAT GGT GTG GGG AAA GTA AAC
TTT ACT GCA GGT GTC GGG GGA TAT CGC TCT AGT CAG GCA TTA GCA ATT
GGT TCT GGC TAT CGT GTA AAT GAG AGT GTC GCA CTT AAA GCC GGT GTG
GCT TAT GCC GGT TCC TCG GAT GTC ATG TAC AAT GCA TCA TTT AAT ATC
GAG TGG taa tag gttt atc ggaccgttccaacttaccgaccagttcggcaggtatg (SEQ ID NO: 3)

FIG. 12 aggaaacagctatgaccatgattacgccaagcttggtacttgtatggattagtcgagctaaaaagctcatatttttatattcaa
actatatacccttcaagctttgaaaaataaacttaattattatatatgttatttagctagttttttaattaaagttaaaatcgagagc
ttgtttgacaaaaaacaaaaaaatttcttgaaaattttttttttgactcaatatctagacttgcaagagcttggaactttgagatt
gttctaagatgcatacaaattcaaaatgcttaaacaaaaataatttaacaaaggagtaagattgttatgaacattcgtccatt
acaagatagagtattagttcgtcgtgca ggt acc atat gtt ttc gcc ctt tct aga ATG AAT AAA GTA
AAA TTT TAT GTT TTA TTT ACG GCG TTA CTA TCC TCT CTA TGT GCA CAC GGA
GCT AGA GAC TAT AAG GAC GAT GAT GAC AAA GAA TTC GGA GCT AGC CCG
CAG TAC CGT GCG GAT ATC GGC GCG TAC ATG GGC AAC CAG TGG ATG GCG
CGC AAC CTG CAA ATG CAG ACC CTC TAT GAC CGC GAG GGC AGC CAG TAT
CGT AAT GCC GAT GGC AGC GTA TGG GCG CGC TTC AAA GCG GGT AAA GCG
GAA TCC GAG GCT GTC AGC GGC AAT ATC GAT ATG GAC AGC AAC TAC TCC
CAG TTC CAG TTA GGC GGC GAC ATT CTG GCC TGG GGT AAC GGC AGC AG
AGC GTT ACC GTT GGC GTC ATG GCG AGC TAC ATC AAC GCC GAT ACC GAC
AGC ACC GGT AAC CGT GGC GCA GAC GGT AGC CAG TTC ACC AGT AGC GGC
AAC GTA GAC GGC TAC AAC CTT GGC GTC TAT GCC ACC TGG TTT GCC GAT
GCC CAA ACG CAT AGC GGC GCG TAT GTC GAC AGC TGG TAC CAA TAT GGT
TTC TAC AAC AAC AGC GTA GAG AGC GGT GAT GCG GGA TCT GAA TCT TAT
GAT TCA ACC GCT AAC GCC GTC TCG CTG GAA ACT GGT TAT CGC TAC GAT
ATT GCG CTT AGC AAC GGT AAT ACT GTC AGT CTG ACG CCG CAG GCG CAG
GTT GTC TGG CAG AAT TAC TCA GCG GAT AGC GTG AAG GAT AAC TAC GGC
ACC CGG ATT GAT GGT CAG GAT GGC GAC AGT TGG ACA ACG CGT CTG GGT
CTG CGT GTT GAC GGC AAG CTG TAC AAA GGC AGC CGT ACG GTT ATC CAG
CCG TTT GCT GAA GCT AAC TGG CTG CAC ACC AGC GAT GAT GTG TCG GTA
TCG TTT GAT GAT GCT ACG GTG AAA CAG GAT CTT CCG GCT AAC CGT GCG
GAG CTG AAA GTG GGT CTG CAG GCA GAT ATC GAT AAG CAG TGG AGC GTT
CGC GCT CAG GTT GCC GGG CAG ACT GGC AGC AAT GAC TTT GGC GAT CTG
AAC GGT AGC CTC AAT CTG CGC TAT AAC TGG ATC CAC tag
ctcgtttcaaattaccgatgatatcggaccgttccaacttaccgaccagttcggcaggtatg (SEQ ID NO: 17)

FIG. 13

<u>aggaaacagctatgacc</u>atgattacgccaagcttggtac*ttgtatggattagtcgagctaaaaagctcatattttttatattcaa*
*actatataccccttcaagctttgaaaaataaacttaattattatatatgttatttagctagttttttttaattaaagttaaaatcgagagc*
*ttgtttgacaaaaaaacaaaaaaatttcttgaaaattttttttttgactcaatatctagacttgcaagagcttggaactttgagatt*
*gttctaagatgcatacaaattcaaaatgcttaaacaaaaataatttaacaaaggagtaagattgttatgaacattcgtccatt*
*acaagatagagtattagttcgtcgtgca* ggt acc atat <u>gtt ttc</u> gcc ctt <u>tct aga</u> ATG AAT AAA GTA
AAA TTT TAT GTT TTA TTT ACG GCG TTA CTA TCC TCT CTA TGT GCA CAC GGA
GCT AGA GAC TAT AAG GAC GAT GAT GAC AAA GAA TTC AAG TTT CTG AAC
ACA GCC AAA GAT CGG AAC CGC TGG GAG GAG CCT GAC CAG CAG CTC TAC
AAC GTA GAG GCC ACA TCC TAC GCC GGG GGA GGT GGG AGC AGC GGA GGA
GGT GGC AGC AGC GCT AGC CCG CAG TAC CGT GCG GAT ATC GGC GCG TAC
ATG GGC AAC CAG TGG ATG GCG CGC AAC CTG CAA ATG CAG ACC CTC TAT
GAC CGC GAG GGC AGC CAG TAT CGT AAT GCC GAT GGC AGC GTA TGG GCG
CGC TTC AAA GCG GGT AAA GCG GAA TCC GAG GCT GTC AGC GGC AAT ATC
GAT ATG GAC AGC AAC TAC TCC CAG TTC CAG TTA GGC GGC GAC ATT CTG
GCC TGG GGT AAC GGC AGC AGC GTT ACC GTT GGC GTC ATG GCG AGC
TAC ATC AAC GCC GAT ACC GAC AGC ACC GGT AAC CGT GGC GCA GAC GGT
AGC CAG TTC ACC AGT AGC GGC AAC GTA GAC GGC TAC AAC CTT GGC GTC
TAT GCC ACC TGG TTT GCC GAT GCC CAA ACG CAT AGC GGC GCG TAT GTC
GAC AGC TGG TAC CAA TAT GGT TTC TAC AAC AAC AGC GTA GAG AGC GGT
GAT GCG GGA TCT GAA TCT TAT GAT TCA ACC GCT AAC GCC GTC TCG CTG
GAA ACT GGT TAT CGC TAC GAT ATT GCG CTT AGC AAC GGT AAT ACT GTC
AGT CTG ACG CCG CAG GCG CAG GTT GTC TGG CAG AAT TAC TCA GCG GAT
AGC GTG AAG GAT AAC TAC GGC ACC CGG ATT GAT GGT CAG GAT GGC GAC
AGT TGG ACA ACG CGT CTG GGT CTG CGT GTT GAC GGC AAG CTG TAC AAA
GGC AGC CGT ACG GTT ATC CAG CCG TTT GCT GAA GCT AAC TGG CTG CAC
ACC AGC GAT GAT GTG TCG GTA TCG TTT GAT GAT GCT ACG GTG AAA CAG
GAT CTT CCG GCT AAC CGT GCG GAG CTG AAA GTG GGT CTG CAG GCA GAT
ATC GAT AAG CAG TGG AGC GTT CGC GCT CAG GTT GCC GGG CAG ACT GGC
AGC AAT GAC TTT GGC GAT CTG AAC GGT AGC CTC AAT CTG CGC TAT AAC
<u>T</u>GG ATC CAC tag ctcgtttcaaattaccgatgatatcggaccgttccaactt<u>accgaccagttcggcaggtatg</u>
(SEQ ID NO: 18)

FIG. 14 aggaaacagctatgaccatgattacgccaagcttggtacttgtatggattagtcgagctaaaaagctcatatttttatattcaaactatata
cccttcaagctttgaaaaataaacttaattattatatatgttatttagctagttttttaattaaagttaaaatcgagagcttgtttgacaaaaaa
acaaaaaaatttcttgaaaattttttttttgactcaatatctagacttgcaagagcttggaactttgagattgttctaagatgcatacaaattca
aaatgcttaaacaaaaataatttaacaaaggagtaagattgttatgaacattcgtccattacaagatagagtattagttcgtcgtgca
ggt acc atat gtt ttc gcc ctt tct aga ATG AAT AAA GTA AAA TTT TAT GTT TTA TTT ACG GCG
TTA CTA TCC TCT CTA TGT GCA CAC GGA GCT AGA GAC TAT AAG GAC GAT GAT GAC
AAA GAA TTC GGG GGG GAA CAG AAC ATG ATT GGC ATG ACA CCA ACA GTC ATT
GCG GTA CAC TAC CTG GAC CAG ACC GAA CAG TGG GAG AAG TTC GGC ATA GAG
AAG AGG CAA GAG GCC CTG GAG CTC ATC AAG AAA GGG TAC ACC CAG CAG CTG
GCC TTC AAA CAG CCC AGC TCT GCC TAT GCT GCC TTC AAC AAC CGG CCC CCC
AGC ACC TGG CTG ACA GCC TAC GTG GTC AAG GTC TTC TCT CTA GCT GCC AAC CTC
ATC GCC ATC GAC TCT CAC GTC CTG TGT GGG GCT GTT AAA TGG TTG ATT CTG GAG
AAA CAG AAG CCG GAT GGT GTC TTT CAG GAG GAT GGG CCC GTG ATT CAC CAA
GAA ATG ATT GGT GGC TTC CGG AAC GCC AAG GAG GCA GAT GTG TCA CTC ACA
GCC TTC GTC CTC ATC GCA CTG CAG GAA GCC AGG GAC ATC TGT GAG GGG CAG
GTC AAT AGC CTT CCT GGG AGC ATC AAC AAG GCA GGG GAG TAT ATT GAA GCC AGT
TAC ATG AAC CTG CAG AGA CCA TAC ACA GTG GCC ATT GCT GGG TAT GCC CTG
GCC CTG ATG AAC AAA CTG GAG GAA CCT TAC CTC GGC AAG TTT CTG AAC ACA GCC
AAA GAT CGG AAC CGC TGG GAG GAG CCT GAC CAG CAG CTC TAC AAC GTA GAG
GCC ACA TCC TAC GCC CTC CTG GCC CTG CTG CTG CTG AAA GAC TTT GAC TCT GTG
CCC CCT GTA GTG CGC TGG CTC AAT GAG CAA AGA TAC TAC GGA GGC GGC TAT
GGC TCC ACC CAG GCT ACC TTC ATG GTA TTC CAA GCC TTG GCC CAA TAT CAA ACA
GAT GTC CCT GAC CAT AAG GAC TTG AAC GGA GGT GCT AGC CCG CAG TAC CGT
GCG GAT ATC GGC GCG TAC ATG GGC AAC CAG TGG ATG GCG CGC AAC CTG CAA
ATG CAG ACC CTC TAT GAC CGC GAG GGC AGC CAG TAT CGT AAT GCC GAT GGC
AGC GTA TGG GCG CGC TTC AAA GCG GGT AAA GCG GAA TCC GAG GCT GTC AGC
GGC AAT ATC GAT ATG GAC AGC AAC TAC TCC CAG TTC CAG TTA GGC GGC GAC ATT
CTG GCC TGG GGT AAC GGC CAG CAG AGC GTT ACC GTT GGC GTC ATG GCG AGC
TAC ATC AAC GCC GAT ACC GAC AGC ACC GGT AAC CGT GGC GCA GAC GGT AGC
CAG TTC ACC AGT AGC GGC AAC GTA GAC GGC TAC AAC CTT GGC GTC TAT GCC
ACC TGG TTT GCC GAT GCC CAA ACG CAT AGC GGC GCG TAT GTC GAC AGC TGG
TAC CAA TAT GGT TTC TAC AAC AAC AGC GTA GAG AGC GGT GAT GCG GGA TCT GAA
TCT TAT GAT TCA ACC GCT AAC GCC GTC TCG CTG GAA ACT GGT TAT CGC TAC GAT
ATT GCG CTT AGC AAC GGT AAT ACT GTC AGT CTG ACG CCG CAG GCG CAG GTT
GTC TGG CAG AAT TAC TCA GCG GAT AGC GTG AAG GAT AAC TAC GGC ACC CGG
ATT GAT GGT CAG GAT GGC GAC AGT TGG ACA ACG CGT CTG GGT CTG CGT GTT
GAC GGC AAG CTG TAC AAA GGC AGC CGT ACG GTT ATC CAG CCG TTT GCT GAA
GCT AAC TGG CTG CAC ACC AGC GAT GAT GTG TCG GTA TCG TTT GAT GAT GCT ACG
GTG AAA CAG GAT CTT CCG GCT AAC CGT GCG GAG CTG AAA GTG GGT CTG CAG
GCA GAT ATC GAT AAG CAG TGG AGC GTT CGC GCT CAG GTT GCC GGG CAG ACT
GGC AGC AAT GAC TTT GGC GAT CTG AAC GGT AGC CTC AAT CTG CGC TAT AAC TGG
ATC CAC tag ctcgtttcaaattaccgatgatatcggaccgttccaacttaccgaccagttcggcaggtatg (SEQ ID NO: 19)

FIG. 15

SEQUENCE LISTING

<160> NUMBER OF SEQ ID NOS: 29

<210> SEQ ID NO 1
<211> LENGTH: 1068
<212> TYPE: DNA
<213> ORGANISM: Artificial Sequence
<220> FEATURE:
<223> OTHER INFORMATION: pYF

<400> SEQUENCE: 1

```
aggaaacagc tatgaccatg attacgccaa gcttggtact tgtatggatt agtcgagcta    60
aaaagctcat atttttata ttcaaactat ataccctttca agctttgaaa ataaaactta   120
attattatat atgttattta gctagttttt ttaattaaag ttaaaatcga gagcttgttt   180
gacaaaaaaa caaaaaaatt tcttgaaaat ttttttttg actcaatatc tagacttgca   240
agagcttgga actttgagat tgttctaaga tgcatacaaa ttcaaaatgc ttaaacaaaa   300
ataatttaac aaaggagtaa gattgttatg aacattcgtc cattacaaga tagagtatta   360
gttcgtcgtg caggtaccat atgaattcac taaagaaata taaaaggtgc ttacaatgac   420
taaagatttt aagatcagtg tctctgcggc attaatatct gcgttgttct catctccata   480
tgcatttgcc aataatgacg agctcgacta taaggacgat gatgacaaat tggatatggc   540
aaaaaaacac tcaaatagtg ttgctagaac aactttagaa actgctgaag aacatacaaa   600
taaaaaatca gctgagacgt tagcaagcgc taatgtgtat gcagacagca agtcttctca   660
cacactaaaa actgcaaata gctataccga tgtgaccgta agtaattcga ctaagaaagc   720
aatccgtgaa tcgaatcaat acacagatca taaattccaa caacttgaca accgtttaga   780
taaacttgac acacgagttg acaaaggttt agccagttca gccgctttaa acagcttgtt   840
ccagccatat ggtgtgggga aagtaaactt tactgcaggt gtcgggggat atcgctctag   900
tcaggcatta gcaattggtt ctggctatcg tgtaaatgag agtgtcgcac ttaaagccgg   960
tgtggcttat gccggttcct cggatgtcat gtacaatgca tcatttaata tcgagtggta  1020
ataggtttat cggaccgttc caacttaccg accagttcgg caggtatg              1068
```

<210> SEQ ID NO 2
<211> LENGTH: 1932
<212> TYPE: DNA
<213> ORGANISM: Artificial Sequence
<220> FEATURE:
<223> OTHER INFORMATION: pYFC

<400> SEQUENCE: 2

```
aggaaacagc tatgaccatg attacgccaa gcttggtact tgtatggatt agtcgagcta    60
```

| | |
|---|---|
| aaaagctcat atttttata ttcaaactat atacccttca agctttgaaa aataaactta | 120 |
| attattatat atgttattta gctagttttt ttaattaaag ttaaaatcga gagcttgttt | 180 |
| gacaaaaaaa caaaaaaatt tcttgaaaat ttttttttg actcaatatc tagacttgca | 240 |
| agagcttgga actttgagat tgttctaaga tgcatacaaa ttcaaaatgc ttaaacaaaa | 300 |
| ataatttaac aaaggagtaa gattgttatg aacattcgtc cattacaaga tagagtatta | 360 |
| gttcgtcgtg caggtaccat atgaattcac taaagaaata taaaaggtgc ttacaatgac | 420 |
| taaagatttt aagatcagtg tctctgcggc attaatatct gcgttgttct catctccata | 480 |
| tgcatttgcc aataatgacg agctcggggg ggaacagaac atgattggca tgacaccaac | 540 |
| agtcattgcg gtacactacc tggaccagac cgaacagtgg gagaagttcg gcatagagaa | 600 |
| gaggcaagag gccctggagc tgatcaagaa agggtacacc cagcagctgg ccttcaaaca | 660 |
| gcccagctct gcctatgctg ccttcaacaa ccggcccccc agcacctggc tgacagccta | 720 |
| cgtggtcaag gtcttctctc tagctgccaa cctcatcgcc atcgactctc acgtcctgtg | 780 |
| tggggctgtt aaatggttga ttctggagaa acagaagccg atggtgtct ttcaggagga | 840 |
| tgggcccgtg attaccaag aaatgattgg tggcttccgg aacgccaagg aggcagatgt | 900 |
| gtcactcaca gccttcgtcc tcatcgcact gcaggaagcc agggacatct gtgaggggca | 960 |
| ggtcaatagc cttcctggga gcatcaacaa ggcaggggag tatattgaag ccagttacat | 1020 |
| gaacctgcag agaccataca cagtggccat tgctgggtat gccctggccc tgatgaacaa | 1080 |
| actggaggaa ccttacctcg gcaagtttct gaacacagcc aaagatcgga accgctggga | 1140 |
| ggagcctgac cagcagctct acaacgtaga ggccacatcc tacgccctcc tggccctgct | 1200 |
| gctgctgaaa gactttgact ctgtgccccc tgtagtgcgc tggctcaatg agcaaagata | 1260 |
| ctacggaggc ggctatggct ccacccaggc taccttcatg gtattccaag ccttggccca | 1320 |
| atatcaaaca gatgtccctg accataagga cttgaacgga ggtgagctcg actataagga | 1380 |
| cgatgatgac aaattggata tggcaaaaaa acactcaaat agtgttgcta gaacaacttt | 1440 |
| agaaactgct gaagaacata caaataaaaa atcagctgag acgttagcaa gcgctaatgt | 1500 |
| gtatgcagac agcaagtctt ctcacacact aaaaactgca aatagctata ccgatgtgac | 1560 |
| cgtaagtaat tcgactaaga aagcaatccg tgaatcgaat caatacacag atcataaatt | 1620 |
| ccatcaactt gacaaccgtt tagataaact tgacacacga gttgacaaag gtttagccag | 1680 |
| ttcagccgct ttaaacagct tgttccagcc atatggtgtg gggaaagtaa actttactgc | 1740 |
| aggtgtcggg ggatatcgct ctagtcaggc attagcaatt ggttctggct atcgtgtaaa | 1800 |
| tgagagtgtc gcacttaaag ccggtgtggc ttatgccggt tcctcggatg tcatgtacaa | 1860 |
| tgcatcattt aatatcgagt ggtaataggt ttatcggacc gttccaactt accgaccagt | 1920 |
| tcggcaggta tg | 1932 |

<210> SEQ ID NO 3
<211> LENGTH: 1194
<212> TYPE: DNA
<213> ORGANISM: Artificial Sequence
<220> FEATURE:
<223> OTHER INFORMATION: pYFP

<400> SEQUENCE: 3

| | |
|---|---|
| aggaaacagc tatgaccatg attacgccaa gcttggtact tgtatggatt agtcgagcta | 60 |
| aaaagctcat atttttata ttcaaactat atacccttca agctttgaaa aataaactta | 120 |
| attattatat atgttattta gctagttttt ttaattaaag ttaaaatcga gagcttgttt | 180 |

```
gacaaaaaaa caaaaaatt tcttgaaaat tttttttttg actcaatatc tagacttgca    240
agagcttgga actttgagat tgttctaaga tgcatacaaa ttcaaaatgc ttaaacaaaa    300
ataatttaac aaaggagtaa gattgttatg aacattcgtc cattacaaga tagagtatta    360
gttcgtcgtg caggtaccat atgaattcac taaagaaata taaaggtgc ttacaatgac    420 taaagatttt aagatcagtg tctctgcggc attaatatct gcgttgttct catctccata    480
tgcatttgcc aataatgacg agctcaagtt tctgaacaca gccaaagatc ggaaccgctg    540
ggaggagcct gaccagcagc tctacaacgt agaggccaca tcctacgccg ggggaggtgg    600
gagcagcgga ggaggtggca gcagcgagct cgactataag gacgatgatg acaaattgga    660
tatggcaaaa aaacactcaa atagtgttgc tagaacaact ttagaaactg ctgaagaaca    720
tacaaataaa aaatcagctg agacgttagc aagcgctaat gtgtatgcag acagcaagtc    780
ttctcacaca ctaaaaactg caaatagcta taccgatgtg accgtaagta attcgactaa    840
gaaagcaatc cgtgaatcga atcaatacac agatcataaa ttccatcaac ttgacaaccg    900
tttagataaa cttgacacac gagttgacaa aggtttagcc agttcagccg ctttaaacag    960
cttgttccag ccatatggtg tggggaaagt aaacttact gcaggtgtcg ggggatatcg    1020
ctctagtcag gcattagcaa ttggttctgg ctatcgtgta aatgagagtg tcgcacttaa    1080
agccggtgtg gcttatgccg gttcctcgga tgtcatgtac aatgcatcat ttaatatcga    1140
gtggtaatag gtttatcgga ccgttccaac ttaccgacca gttcggcagg tatg          1194

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
gaattcacta aagaaatata aaaggtgctt aca                                  33

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gagctcgtca ttattggcaa atgc                                            24

<210> SEQ ID NO 6
<211> LENGTH: 59
<212> TYPE: DNA
<213> ORGANISM: Artificial Sequence
<220> FEATURE:
<223> OTHER INFORMATION: primer

<400> SEQUENCE: 6
gagctcgact ataaggacga tgatgacaaa ttggatatgg caaaaaaaca ctcaaatag      59

<210> SEQ ID NO 7
<211> LENGTH: 38
<212> TYPE: DNA
<213> ORGANISM: Artificial Sequence
<220> FEATURE:
<223> OTHER INFORMATION: primer
```

<400> SEQUENCE: 7
gtttaaacct attaccactc gatattaaat gatgcatt                              38

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
catacctgcc gaactggtcg g                                                21

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
accggtgggg gggaacagaa catgattggc atg                                   33

<210> SEQ ID NO 10
<211> LENGTH: 39
<212> TYPE: DNA
<213> ORGANISM: Artificial Sequence
<220> FEATURE:
<223> OTHER INFORMATION: primer

<400> SEQUENCE: 10
gtcgacggac ccgggacctc cgttcaagtc cttatggtc                             39

<210> SEQ ID NO 11
<211> LENGTH: 34
<212> TYPE: DNA
<213> ORGANISM: Artificial Sequence
<220> FEATURE:
<223> OTHER INFORMATION: primer

<400> SEQUENCE: 11
gcaagaggcc ctggagctga tcaagaaagg gtac                                  34

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12 gtacccttc ttgatcagct ccagggcctc ttgc                                   34

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
gagctcgggg gggaacagaa catgattgg                                        29

<210> SEQ ID NO 14
<211> LENGTH: 30

```
<212> TYPE: DNA
<213> ORGANISM: Artificial Sequence
<220> FEATURE:
<223> OTHER INFORMATION: primer

<400> SEQUENCE: 14
gagctcacct ccgttcaagt ccttatggtc                                          30

<210> SEQ ID NO 15
<211> LENGTH: 80
<212> TYPE: DNA
<213> ORGANISM: Artificial Sequence
<220> FEATURE:
<223> OTHER INFORMATION: primer

<400> SEQUENCE: 15
ttggagctca gtttctgaa cacagccaaa gatcggaacc gctgggagga gcctgaccag          60
cagctctaca acgtagaggc                                                    80

<210> SEQ ID NO 16
<211> LENGTH: 81
<212> TYPE: DNA
<213> ORGANISM: Artificial Sequence
<220> FEATURE:
<223> OTHER INFORMATION: primer

<400> SEQUENCE: 16
tccgagctcg ctgctgccac ctcctccgct gctcccacct cccccggcgt aggatgtggc         60
ctctacgttg tagagctgct g                                                  81

<210> SEQ ID NO 17
<211> LENGTH: 1524
<212> TYPE: DNA
<213> ORGANISM: Artificial Sequence
<220> FEATURE:
<223> OTHER INFORMATION: plasmid pSF

<400> SEQUENCE: 17
aggaaacagc tatgaccatg attacgccaa gcttggtact tgtatggatt agtcgagcta         60
aaaagctcat atttttata ttcaaactat atacccttca agctttgaaa ataaactta         120 attattatat atgttattta gctagttttt ttaattaaag ttaaaatcga gagcttgttt        180
gacaaaaaaa caaaaaaatt tcttgaaaat ttttttttg actcaatatc tagacttgca        240
agagcttgga actttgagat tgttctaaga tgcatacaaa ttcaaaatgc ttaaacaaaa        300
ataatttaac aaaggagtaa gattgttatg aacattcgtc cattcaaga tagagtatta        360 gttcgtcgtg caggtaccat atgttttcgc cctttctaga atgaataaag taaaattta        420 tgttttattt acggcgttac tatcctctct atgtgcacac ggagctagag actataagga        480
cgatgatgac aaagaattcg gagctagccc gcagtaccgt gcggatatcg gcgcgtacat        540
gggcaaccag tggatggcgc gcaacctgca aatgcagacc ctctatgacc gcgagggcag        600
ccagtatcgt aatgccgatg gcagcgtatg ggcgcgcttc aaagcgggta agcggaatc        660 cgaggctgtc agcggcaata tcgatatgga cagcaactac tcccagttcc agttaggcgg        720
cgacattctg gcctggggta acggccagca gagcgttacc gttggcgtca tggcgagcta        780
catcaacgcc gataccgaca gcaccggtaa ccgtggcgca gacggtagcc agttcaccag        840
tagcggcaac gtagacggct acaaccttgg cgtctatgcc acctggtttg ccgatgccca        900
aacgcatagc ggcgcgtatg tcgacagctg gtaccaatat ggtttctaca caacagcgt         960
```

| agagagcggt gatgcgggat ctgaatctta tgattcaacc gctaacgccg tctcgctgga | 1020 |
| aactggttat cgctacgata ttgcgcttag caacggtaat actgtcagtc tgacgccgca | 1080 |
| ggcgcaggtt gtctggcaga attactcagc ggatagcgtg aaggataact acggcacccg | 1140 |
| gattgatggt caggatggcg acagttggac aacgcgtctg gtctgcgtg ttgacggcaa | 1200 |
| gctgtacaaa ggcagccgta cggttatcca gccgtttgct gaagctaact ggctgcacac | 1260 |
| cagcgatgat gtgtcggtat cgtttgatga tgctacggtg aaacaggatc ttccggctaa | 1320 |
| ccgtgcggag ctgaaagtgg gtctgcaggc agatatcgat aagcagtgga gcgttcgcgc | 1380 |
| tcaggttgcc gggcagactg gcagcaatga ctttggcgat ctgaacggta gcctcaatct | 1440 |
| gcgctataac tggatccact agctcgtttc aaattaccga tgatatcgga ccgttccaac | 1500 |
| ttaccgacca gttcggcagg tatg | 1524 |

<210> SEQ ID NO 18
<211> LENGTH: 1641
<212> TYPE: DNA
<213> ORGANISM: Artificial Sequence
<220> FEATURE:
<223> OTHER INFORMATION: plasmid pSPF

<400> SEQUENCE: 18

| aggaaacagc tatgaccatg attacgccaa gcttggtact tgtatggatt agtcgagcta | 60 |
| aaaagctcat atttttata ttcaaactat atacccttca agctttgaaa ataaacttta | 120 |
| attattatat atgttattta gctagttttt ttaattaaag ttaaaatcga gagcttgttt | 180 |
| gacaaaaaaa caaaaaaatt tcttgaaaat ttttttttg actcaatatc tagacttgca | 240 |
| agagcttgga actttgagat tgttctaaga tgcatacaaa ttcaaaatgc ttaaacaaaa | 300 |
| ataatttaac aaaggagtaa gattgttatg aacattcgtc cattacaaga tagagtatta | 360 |
| gttcgtcgtg caggtaccat atgttttcgc cctttctaga atgaataaag taaaattta | 420 |
| tgttttattt acgcgttac tatcctctct atgtgcacac ggagctagag actataagga | 480 |
| cgatgatgac aaagaattca gtttctgaa cacagccaaa gatcggaacc gctgggagga | 540 |
| gcctgaccag cagctctaca acgtagaggc cacatcctac gccgggggag gtgggagcag | 600 |
| cggaggaggt ggcagcagcg ctagcccgca gtaccgtgcg gatatcggcg cgtacatggg | 660 |
| caaccagtgg atggcgcgca acctgcaaat gcagaccctc tatgaccgcg agggcagcca | 720 |
| gtatcgtaat gccgatggca cgtatgggc gcgcttcaaa gcgggtaaag cggaatccga | 780 |
| ggctgtcagc ggcaatatcg atatggacag caactactcc cagttccagt taggcggcga | 840 |
| cattctggcc tgggtaacg gccagcagag cgttaccgtt ggcgtcatgg cgagctacat | 900 |
| caacgccgat accgacagca ccggtaaccg tggcgcagac ggtagccagt tcaccagtag | 960 |
| cggcaacgta gacggctaca accttggcgt ctatgccacc tggtttgccg atgcccaaac | 1020 |
| gcatagcggc gcgtatgtcg acagctggta ccaatatggt ttctacaaca acagcgtaga | 1080 |
| gagcggtgat gcgggatctg aatcttatga ttcaaccgct aacgccgtct cgctggaaac | 1140 |
| tggttatcgc tacgatattg cgcttagcaa cggtaatact gtcagtctga cgccgcaggc | 1200 |
| gcaggttgtc tggcagaatt actcagcgga tagcgtgaag gataactacg gcacccggat | 1260 |
| tgatggtcag gatggcgaca gttggacaac gcgtctgggt ctgcgtgttg acggcaagct | 1320 |
| gtacaaaggc agccgtacgg ttatccagcc gtttgctgaa gctaactggc tgcacaccag | 1380 |
| cgatgatgtg tcggtatcgt ttgatgatgc tacggtgaaa caggatcttc cggctaaccg | 1440 |
| tgcggagctg aaagtgggtc tgcaggcaga tatcgataag cagtggagcg ttcgcgctca | 1500 |

| | | | | |
|---|---|---|---|---|
| ggttgccggg | cagactggca | gcaatgactt | tggcgatctg | aacggtagcc tcaatctgcg | 1560 |
| ctataactgg | atccactagc | tcgtttcaaa | ttaccgatga | tatcggaccg ttccaactta | 1620 |
| ccgaccagtt | cggcaggtat | g | | | 1641 |

<210> SEQ ID NO 19
<211> LENGTH: 2379
<212> TYPE: DNA
<213> ORGANISM: Artificial Sequence
<220> FEATURE:
<223> OTHER INFORMATION: plasmid pSCF

<400> SEQUENCE: 19

| | | | | | |
|---|---|---|---|---|---|
| aggaaacagc | tatgaccatg | attacgccaa | gcttggtact | tgtatggatt | agtcgagcta | 60 |
| aaaagctcat | atttttata | ttcaaactat | atacccttca | agctttgaaa | aataaactta | 120 |
| attattatat | atgttattta | gctagttttt | ttaattaaag | ttaaaatcga | gagcttgttt | 180 |
| gacaaaaaaa | caaaaaaatt | tcttgaaaat | ttttttttg | actcaatatc | tagacttgca | 240 |
| agagcttgga | actttgagat | tgttctaaga | tgcatacaaa | ttcaaaatgc | ttaaacaaaa | 300 |
| ataatttaac | aaaggagtaa | gattgttatg | aacattcgtc | cattacaaga | tagagtatta | 360 |
| gttcgtcgtg | caggtaccat | atgttttcgc | cctttctaga | atgaataaag | taaaatttta | 420 |
| tgttttattt | acggcgttac | tatcctctct | atgtgcacac | ggagctagag | actataagga | 480 |
| cgatgatgac | aaagaattcg | gggggaaca | gaacatgatt | ggcatgacac | caacagtcat | 540 |
| tgcggtacac | tacctggacc | agaccgaaca | gtgggagaag | ttcggcatag | agaagaggca | 600 |
| agaggccctg | gagctcatca | agaaagggta | cacccagcag | ctggccttca | acagcccag | 660 |
| ctctgcctat | gctgccttca | caaccggcc | ccccagcacc | tggctgacag | cctacgtggt | 720 |
| caaggtcttc | tctctagctg | ccaacctcat | cgccatcgac | tctcacgtcc | tgtgtgggc | 780 |
| tgttaaatgg | ttgattctgg | agaaacagaa | gccggatggt | gtctttcagg | aggatgggcc | 840 |
| cgtgattcac | caagaaatga | ttggtggctt | ccggaacgcc | aaggaggcag | atgtgtcact | 900 |
| cacagccttc | gtcctcatcg | cactgcagga | agccagggac | atctgtgagg | gcaggtcaa | 960 |
| tagccttcct | gggagcatca | caaggcagg | ggagtatatt | gaagccagtt | acatgaacct | 1020 |
| gcagagacca | tacacagtgg | ccattgctgg | gtatgccctg | gccctgatga | acaaactgga | 1080 |
| ggaaccttac | ctcggcaagt | ttctgaacac | agccaaagat | cggaaccgct | gggaggagcc | 1140 |
| tgaccagcag | ctctacaacg | tagaggccac | atcctacgcc | ctcctggccc | tgctgctgct | 1200 |
| gaaagacttt | gactctgtgc | ccctgtagt | gcgctggctc | aatgagcaaa | gatactacgg | 1260 |
| aggcggctat | ggctccaccc | aggctacctt | catggtattc | caagccttgg | cccaatatca | 1320 |
| aacagatgtc | cctgaccata | aggacttgaa | cggaggtgct | agcccgcagt | accgtgcgga | 1380 |
| tatcggcgcg | tacatgggca | accagtggat | ggcgcgcaac | ctgcaaatgc | agaccctcta | 1440 |
| tgaccgcgag | ggcagccagt | atcgtaatgc | cgatggcagc | gtatgggcgc | gcttcaaagc | 1500 |
| gggtaaagcg | gaatccgagg | ctgtcagcgg | caatatcgat | atggacagca | actactccca | 1560 |
| gttccagtta | ggcggcgaca | ttctggcctg | gggtaacggc | cagcagagcg | ttaccgttgg | 1620 |
| cgtcatggcg | agctacatca | acgccgatac | cgacagcacc | ggtaaccgtg | gcgcagacgg | 1680 |
| tagccagttc | accagtagcg | gcaacgtaga | cggctacaac | cttggcgtct | atgccacctg | 1740 |
| gtttgccgat | gcccaaacgc | atagcggcgc | gtatgtcgac | agctggtacc | aatatggttt | 1800 |
| ctacaacaac | agcgtagaga | gcggtgatgc | gggatctgaa | tcttatgatt | caaccgctaa | 1860 |

```
cgccgtctcg ctggaaactg gttatcgcta cgatattgcg cttagcaacg gtaatactgt      1920
cagtctgacg ccgcaggcgc aggttgtctg gcagaattac tcagcggata gcgtgaagga      1980
taactacggc acccggattg atggtcagga tggcgacagt tggacaacgc gtctgggtct      2040
gcgtgttgac ggcaagctgt acaaaggcag ccgtacggtt atccagccgt ttgctgaagc      2100
taactggctg cacaccagcg atgatgtgtc ggtatcgttt gatgatgcta cggtgaaaca      2160
ggatcttccg gctaaccgtg cggagctgaa agtgggtctg caggcagata tcgataagca      2220
gtggagcgtt cgcgctcagg ttgccgggca gactggcagc aatgactttg gcgatctgaa      2280
cggtagcctc aatctgcgct ataactggat ccactagctc gtttcaaatt accgatgata      2340
tcggaccgtt ccaacttacc gaccagttcg gcaggtatg                             2379

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
gaattcggag ctagcccgca gtaccgtgcg gatatc                                36

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
gctaagggat ccagttatag cgcagattga ggctac                                36

<210> SEQ ID NO 22
<211> LENGTH: 62
<212> TYPE: DNA
<213> ORGANISM: Artificial Sequence
<220> FEATURE:
<223> OTHER INFORMATION: primer

<400> SEQUENCE: 22
tctagaatga ataaagtaaa attttatgtt ttatttacgg cgttactatc ctctctatgt      60
gc                                                                    62

<210> SEQ ID NO 23
<211> LENGTH: 68
<212> TYPE: DNA
<213> ORGANISM: Artificial Sequence
<220> FEATURE:
<223> OTHER INFORMATION: primer

<400> SEQUENCE: 23
gaattctttg tcatcatcgt ccttatagtc tctagctccg tgtgcacata gagaggatag      60
taacgccg                                                              68

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
```

```
gcaggtacca tatgttttcg ccctttctag                                              30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
ctagaaaggg cgaaaacata tggtacctgc                                              30

<210> SEQ ID NO 26
<211> LENGTH: 80
<212> TYPE: DNA
<213> ORGANISM: Artificial Sequence
<220> FEATURE:
<223> OTHER INFORMATION: primer

<400> SEQUENCE: 26
ttggaattca gtttctgaa cacagccaaa gatcggaacc gctgggagga gcctgaccag             60
cagctctaca acgtagaggc                                                         80

<210> SEQ ID NO 27
<211> LENGTH: 81
<212> TYPE: DNA
<213> ORGANISM: Artificial Sequence
<220> FEATURE:
<223> OTHER INFORMATION: primer

<400> SEQUENCE: 27
tccgctagcg ctgctgccac ctcctccgct gctcccacct ccccggcgt aggatgtggc             60 ctctacgttg tagagctgct g                                                       81

<210> SEQ ID NO 28
<211> LENGTH: 33
<212> TYPE: DNA
<213> ORGANISM: Artificial Sequence
<220> FEATURE:
<223> OTHER INFORMATION: primer

<400> SEQUENCE: 28
gaattcgggg gggaacagaa catgattggc atg                                          33

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
gctagcacct ccgttcaagt ccttatggtc                                              30
```

AUTOTRANSPORTER-MEDIATED DISPLAY OF COMPLEMENT RECEPTOR LIGANDS BY BACTERIAL IMMUNOGENS

STATEMENT REGARDING FEDERAL SPONSORED RESEARCH OR DEVELOPMENT

This invention was made with government support under Grant Nos. RO1 AI100138 and RO1 AI123129 awarded by the National Institutes of Health (NIH) and under Grant No. W81XWH1910661 awarded by the Department of Defense (DoD). The government has certain rights in the invention.

CROSS-REFERENCE TO RELATED APPLICATIONS

The present application claims priority to U.S. Provisional No. 62/909,314, filed on Oct. 2, 2019.

BACKGROUND OF THE INVENTION

1. Field of the Invention

The present invention relates to bacteria-based vaccines and, more specifically, to an approach for modifying gram-negative bacteria to increase the vaccine efficacy of the modified bacteria when used as an immunogen.

2. Description of the Related Art

When a monoclonal antibody (mAb) specific for the lipopolysaccharide (LPS) of *Francisella tularensis* (Ft) was added to inactivated Ft (iFt), the resulting mAb-iFt LVS immunogen was targeted to Fc receptors (FcR) to enhance antigen (Ag) processing, presentation, and immunity to challenge against LVS (Live Vaccine Strain) and human-virulent SchuS4. While this approach was effective, it depended on having a pre-existing mAb—a situation that would likely not be the case for an emerging pathogen.

One approach for overcoming this problem was to achieve bacterial targeting through a genetic approach. A self-replicating plasmid that could be transformed into a bacterium could result in a targeted bacterium for use as a vaccine immunogen. Although it would have been desirable to clone the Fc domain of IgG as a fusion to a bacterial outer membrane (OM) protein, thereby mimicking the FcR-targeting effect of surface-bound Ab, the technical challenges of expressing a functional, disulfide-linked and glycosylated Fc domain on the surface(s) of multiple gram-negative bacteria (without specialized modification of each bacterium) were prohibitive. As a result, alternative ligand-receptor pairings would be more amenable to the goal, so work has pursued C3d-CR interactions.

C3d is a known ligand of complement receptor two (CR2) which is found on B-cells and follicular dendritic cells (FDCs). C3d gained significant interest as a "molecular adjuvant" following the demonstration that purified proteins linked to C3d multimers were more potent inducers of Ab than the proteins alone. C3d had not previously been genetically engineered on the surface of an intended whole-cell immunogen. In initial plasmid development efforts, it was determined that genetic fusion of murine C3d to a Ft outer membrane (OM) lipoprotein (Tul4) resulted in surface-displayed C3d and that Ft expressing Tul4-C3d provided enhanced vaccine efficacy. The expression cassette encoding the Tul4-C3d fusion is described in U.S. Pat. No. 9,475,853. While this approach was successful, translation of this technology to other bacteria requires modifications to the plasmid platform. Accordingly, there is a need in the art for an approach that can readily modify different bacteria while continuing to increase the vaccine efficacy of the modified bacteria when used as immunogens.

BRIEF SUMMARY OF THE INVENTION

The present invention is an approach that can be rapidly applied to multiple types of bacteria to produce surface modifications that enhance the immunologic response when the bacteria is used as a vaccine. The present invention comprises a series of plasmids (pYF, pYFC, pYFP, pSF, pSPF, and pSCF); pYFC- pYFP-, pSPF-, and pSCF-transformed bacteria are targeted to complement receptors (CR) on antigen presenting cells (APC). When bacteria modified according to the present invention as a vaccine, the vaccine recipient produces significantly higher titers of specific antibodies and are better protected against challenges from the wild-type, disease-causing agent of interest.

More specifically, in a first embodiment, the present invention comprises a platform for improving the immunologic response of a bacterial vaccine. The platform comprises a plasmid having a first nucleic acid region that encodes a cleavable, N-terminal signal sequence (SS), second and third nucleic acid sequences encoding at least a portion of a ligand for complement receptor two (CR2) or complement receptor three (CR3), and a protein tag, and a fourth nucleic acid sequence encoding a C-terminal, β-barrel OM-insertion domain of an autotransporter. The plasmid may have a sequence selected from group consisting of SEQ ID NO: 1, SEQ ID NO: 2, SEQ ID NO: 3, SEQ ID NO: 17, SEQ ID NO: 18, SEQ ID NO: 19. The autotransporter may comprise a trimeric *Yersinia* adhesion protein A (YadA) or a monomeric *Salmonella* adhesin protein A (ShdA). The ligand may comprise complement component C3d. The ligand may also comprise complement receptor-binding peptide p28. The protein tag may comprise a FLAG tag.

In another embodiment, the present invention comprises a bacteria containing a plasmid having a first nucleic acid region that encodes a cleavable, N-terminal signal sequence (SS), second and third nucleic acid sequences encoding at least a portion of a ligand for complement receptor two (CR2) or complement receptor three (CR3), and a protein tag, and a fourth nucleic acid sequence encoding a C-terminal, β-barrel OM-insertion domain of an autotransporter. The plasmid may have a sequence selected from group consisting of SEQ ID NO: 1, SEQ ID NO: 2, SEQ ID NO: 3, SEQ ID NO: 17, SEQ ID NO: 18, SEQ ID NO: 19. The autotransporter may comprise a trimeric *Yersinia* adhesion protein A (YadA) or a monomeric *Salmonella* adhesin protein A (ShdA). The ligand may comprise complement component C3d. The ligand may also comprise complement receptor-binding peptide p28. The protein tag may comprise a FLAG tag.

In a further embodiment, the present invention is a method of improving the immunologic response of a bacterial vaccine. The method comprises the steps of obtaining an amount of bacteria for use as a bacterial vaccine and transforming the amount of bacteria with a plasmid having a first nucleic acid region that encodes a cleavable, N-terminal signal sequence (SS), second and third nucleic acid sequences encoding at least a portion of a ligand for complement receptor two (CR2) or complement receptor three (CR3), and a protein tag, and a fourth nucleic acid sequence encoding a C-terminal, β-barrel OM-insertion domain of an autotransporter. The plasmid may have a sequence selected from group consisting of SEQ ID NO: 1, SEQ ID NO: 2, SEQ ID NO: 3, SEQ ID NO: 17, SEQ ID NO: 18, SEQ ID NO: 19. The autotransporter may comprise a trimeric *Yersinia* adhesion protein A (YadA) or a monomeric *Salmonella* adhesin protein A (ShdA). The ligand may comprise complement component C3d. The ligand may also comprise complement receptor-binding peptide p28. The protein tag may comprise a FLAG tag.

BRIEF DESCRIPTION OF THE SEVERAL VIEWS OF THE DRAWING(S)

Figure 2:
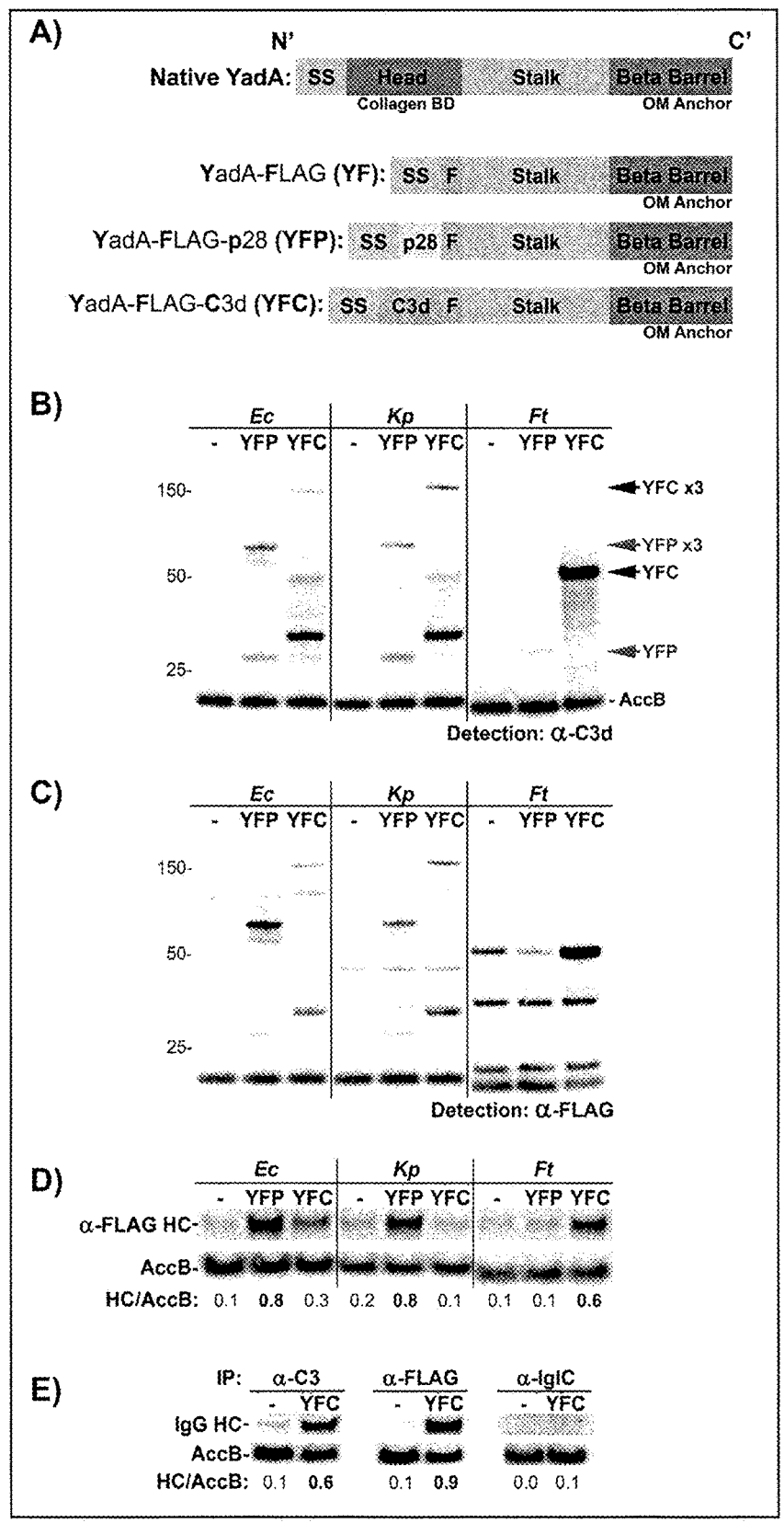

The present invention will be more fully understood and appreciated by reading the following Detailed Description in conjunction with the accompanying drawings, in which:

FIG. 1 is a schematic of bacterial modification according to the present invention;

FIG. 2 contains the schematics of the domain architectures (A) for three YadA—fusion proteins (YF, YFP, and YFC) according to the present invention as well as biochemical analysis (B-E) of YFP and YFC in *Escherichia coli* (Ec), *Klebsiella pneumoniae* (Kp), and *Francisella tularensis* (Ft). Whole cell lysates of Ec, Kp, and Ft containing empty vector (−) or the YFP or YFC expression vectors were probed by western blot with primary antibody (Ab) specific for C3d (B) or the FLAG epitope (C) followed sequentially by biotinylated secondary Abs and streptavidin-HRP (SA-HRP). YFC and YFP trimers and monomers are designated with black and grey arrows. The ~20 kDa bands evident in all lanes are endogenously biotinylated bacterial proteins (annotated AccB in Ec and Ft) detected by SA-HRP. Intact bacteria as indicated were incubated in solution with α-FLAG Ab and used to immunoprecipitate bound Ab (D). Intact Ft as indicated were incubated in solution with the indicated Ab (E). IglC is primarily a cytoplasmic Ft protein. Washed bacteria in (D) and (E) were probed by for IgG heavy chain (HC) followed by biotinylated secondary Abs and SA-HRP;

FIG. 3 contains the schematics of the domain architectures (A) for three ShdA—fusion proteins (SF, SPF, and SCF) according to the present invention as well as biochemical analysis (B-C) of SPF and SCF in Ec and *Shigella flexneri*. Whole cell lysates of Ec containing empty vector (−) or the SF, SPF, of SCF expression vectors were probed by western blot with primary Ab specific for the FLAG epitope or C3d protein as indicated (B) followed sequentially by biotinylated secondary Abs and streptavidin-HRP (SA-HRP). Whole cell lysates of *Shigella flexneri* containing empty vector (−) or the YFP, YCF, or SPF expression vectors were probed by western blot with primary Ab specific for the FLAG epitope (C) followed sequentially by biotinylated secondary Abs and streptavidin-HRP (SA-HRP). White arrows indicate monomers and black arrows indicate trimers;

FIG. 4 contains graphs, micrographs, and western blots showing that the expression of YFC by Ft (black bars) significantly enhances binding and uptake by CR3-positive RAW cells compared to Ft harboring the empty vector (−) control (white bars). SYTO-stained Ft strains (− and YFC) were incubated at various MOIs with RAW cells for 2 h at 4° C. to assess binding (a) or at 37° C. to allow for bacterial uptake (c). For microscopy images (insets), MOI=100 and scale bars (bottom right) are 50 μm. Quantification of cell association was calculated as the SYTO signal bound to washed RAW cells divided by the total input SYTO signal (of unwashed Ft and cells) at each MOI. *t test $p<0.05$. Results are combined from 4 independent experiments; means shown with standard deviation (SD). Un-stained Ft (− and YFC) were incubated with RAW cells at MOI=0 ("no Ft") or 500 for 2 h at 4° C. (b) or at 37° C. (d). Following washes to remove un-bound bacteria, cell-associated material was probed by western blot with Ab specific for the Ft protein FopA and the cellular protein β-actin;

FIG. 5 is a series of western blots and densitometric analysis demonstrating that YFC-expressing Ft are more potent activators of p38 and p65 phosphorylation in RAW cells. (a) RAW cells were incubated without ("no Ft") or with Ft:− or Ft:YFC (MOI=500) at 37° C. for the indicated time. Washed cells were probed by western blot with Abs specific for the indicated proteins. (b, c) Densitometry of phosphorylated and total forms of p38 and p65 combined from ≥3 independent experiments. *t test $p<0.05$;

FIG. 6 is a survival curve of Balb/c mice that were intranasally-vaccinated according to the present invention once on day 0 with 200 CFU of live Ft LVS bearing pF or pYFC and then challenged i.n. on day 28 with 50,000 CFU of Ft LVS and monitored for 3 weeks;

FIG. 7A and FIG. 7B contain graphs revealing that vaccination of C57BL/6 mice with YFC-bacteria according to the present invention induces higher titers of serum Ab. FIG. 7A is individual mouse weights recorded daily and expressed as a percentage of their baseline weight (average of d −3-0). 7-8 mice per group. # indicates t test $p<0.01$ "−" vs YFC, low doses. * indicates t test $p<0.01$ comparing the high doses. FIG. 7B shows sera were collected on d21 post-vaccination and Ft-specific titers were determined via ELISA. Two-way ANOVA was used to assess the effect of YFC. 7-8 mice per group;

FIGS. 8A through 8G demonstrate that vaccination with YFC-bacteria according to the present invention alters Ag recognition and limits challenge-induced morbidity. FIG. 8A shows individual C57BL/6 mouse weights recorded daily and expressed as a percent of their baseline weight (average of d −3-0); 8 PBS mice and 15-16 mice per vaccine group. * indicates t test $p<0.01$ comparing Ft:− and Ft:YFC. FIG. 8B shows sera collected 21 d PV was assessed by ELISA for Ft-specific Ig, IgG, and IgG2c titers. P values derived from t tests of "−" vs YFC. FIG. 8C shows PV sera pooled from "−" or YFC vaccinated mice were used at equal dilution to test for immunoprecipitation by intact Ft LVS. Washed bacteria were probed via western blot for Ig HC. FIG. 8D shows PV sera pooled from mice vaccinated with "−" or YFC were used at equal titers to probe by western blot aqueous (A), detergent (D), sarkosyl soluble (SS), and sarkosyl insoluble (SI) phases of WT Ft LVS. FIG. 8E shows PV sera from individual mice vaccinated with "−" or YFC were used at equal titers to probe by western blot A phases of WT Ft LVS. FIG. 8F shows mice were challenged i.n. with 12 k or 48 k CFU of WT Ft LVS on d 28 PV. Individual post-challenge mouse weights recorded daily and expressed as a percent of their baseline weight (average of d 26-28 PV) with 4-6 mice per group. #t test $p<0.01$ between "−" and YFC at the 12 k dose. *t test $p<0.01$ between "−" and YFC at the 48 k dose. FIG. 8G shows sera collected on d 21 PC was analyzed by ELISA along with PV sera for total Ft-specific Ig titers. *ANOVA with Tukey post-test $p<0.01$ between indicated groups. Fold-increase (PC/PV) of average titer for each group is indicated in parentheses;

FIG. 9 reveals that C57BL/6 mice vaccinated with YFC-bacteria according to the present invention display improved weight-gain following heterologous challenge. (a) Ft:− and Ft:YFC vaccinated mice were challenged intranasally with Ft LVS RML. Individual post-challenge mouse weights are expressed as a percent of their baseline weight (average of d 26-28 PV) with 7-8 mice per group. *t test p<0.05 between "–" and YFC for $10^5$ challenge dose. (b) Sera collected on d 21 PC was analyzed by ELISA along with PV sera for total Ft-specific Ig titers. *ANOVA with Tukey post-test p<0.05 between indicated groups. Fold-increase (PC/PV) of average titer is indicated in parentheses;

FIG. 10 is a graphic showing the salient sequence features of pYF (SEQ ID NO: 1), showing the following: Non-coding sequence—lower case; Coding sequence—upper-case. Start and stop codons—bold. *Francisella* groEL promoter sequence—italics, native *Yersinia* sequence—grey, FLAG sequence—double underline. Single underlined—notable restriction enzyme sites; thick underline—primer sequences;

FIG. 11 is a graphic showing the salient sequence features of pYFC (SEQ ID NO: 2), showing the following: Non-coding sequence—lower case; Coding sequence—upper-case; Start and stop codons—bold. *Francisella* groEL promoter sequence—italics. Native *Yersinia* sequence—grey; Complement receptor ligand sequence—dashed underline/ light grey, FLAG sequence—double underline. Single underlined—notable restriction enzyme sites; thick underline—primer sequences;

FIG. 12 is a graphic showing the salient sequence features of pYFP (SEQ ID NO: 3), showing the following: Non-coding sequence—lower case; Coding sequence—upper-case; Start and stop codons—bold. *Francisella* groEL promoter sequence—italics. Native *Yersinia* sequence—grey; Complement receptor ligand sequence—dashed underline/ light grey, FLAG sequence—double underline. Single underlined—notable restriction enzyme sites; thick underline—primer sequences;

FIG. 13 is a graphic showing the salient sequence features of pSF (SEQ ID NO: 17), showing the following: Non-coding sequence—lower case; Coding sequence—upper-case; Start and stop codons—bold. *Francisella* groEL promoter sequence—italics. LTB (Ec heat-labile enterotoxin B) signal sequence—dotted underline. FLAG sequence—double underline, native *Salmonella* ShdA sequence—grey. Single underlined—notable restriction enzyme sites; thick underline—primer sequences;

FIG. 14 is a graphic showing the salient sequence features of pSPF (SEQ ID NO: 18), showing the following: Non-coding sequence—lower case; Coding sequence—upper-case; Start and stop codons—bold. *Francisella* groEL promoter sequence—italics. LTB (Ec heat-labile enterotoxin B) signal sequence—dotted underline. FLAG sequence—double underline, Complement receptor ligand sequence—dashed underline/light grey, native *Salmonella* ShdA sequence—grey. Single underlined—notable restriction enzyme sites; thick underline—primer sequences; and FIG. 15 is a graphic showing the salient sequence features of pSCF (SEQ ID NO: 19), showing the following: Non-coding sequence—lower case; Coding sequence—upper-case; Start and stop codons—bold. *Francisella* groEL promoter sequence—italics. LTB (Ec heat-labile enterotoxin B) signal sequence—dotted underline. FLAG sequence—double underline, Complement receptor ligand sequence—dashed underline/light grey, native *Salmonella* ShdA sequence—grey. Single underlined—notable restriction enzyme sites; thick underline—primer sequences.

DETAILED DESCRIPTION OF THE INVENTION

Referring to the figures, wherein like numeral refer to like parts throughout, there is seen in FIG. 1 a CR-targeting platform that produces modifications to bacteria to target CRs on antigen-presenting cells (APC). The OM-topographies are produced by the plasmids pYFC, pYFP, pSCF, and pSFP that code for fusion proteins which can be expressed by multiple types of bacteria to enhance the immunologic response when those types of bacteria are used as vaccines.

The broadly applicable CR-targeting platform employs the C-terminal, β-barrel OM-insertion domains of monomeric and trimeric autotransporters (AT) to display C3d or p28 on bacterial surfaces, as seen in FIG. 1. ATs are a class of gram-negative OMPs whose transport and insertion into the OM is widely-conserved and largely self-directed resulting in surface exposure of the "passenger domain"—which has been engineered here to be a CR-ligand. The relative independence of these proteins lends utility to their use in multiple, gram-negative pathogens. C3d (or p28) has been linked, along with a FLAG tag, to the N-termini of the β-barrel, OM domains from two ATs: the trimeric *Yersinia enterolitica* adhesion protein A (YadA) and the monomeric *Salmonella* adhesion protein A (ShdA). The intent of the trimer is that clusters of surface-C3d should increase avidity for CRs and potentially cross-link these receptors to enhance responses. The monomer approach (lacking the trimeric clusters) is anticipated to provide a more tempered response.

Figure 3:
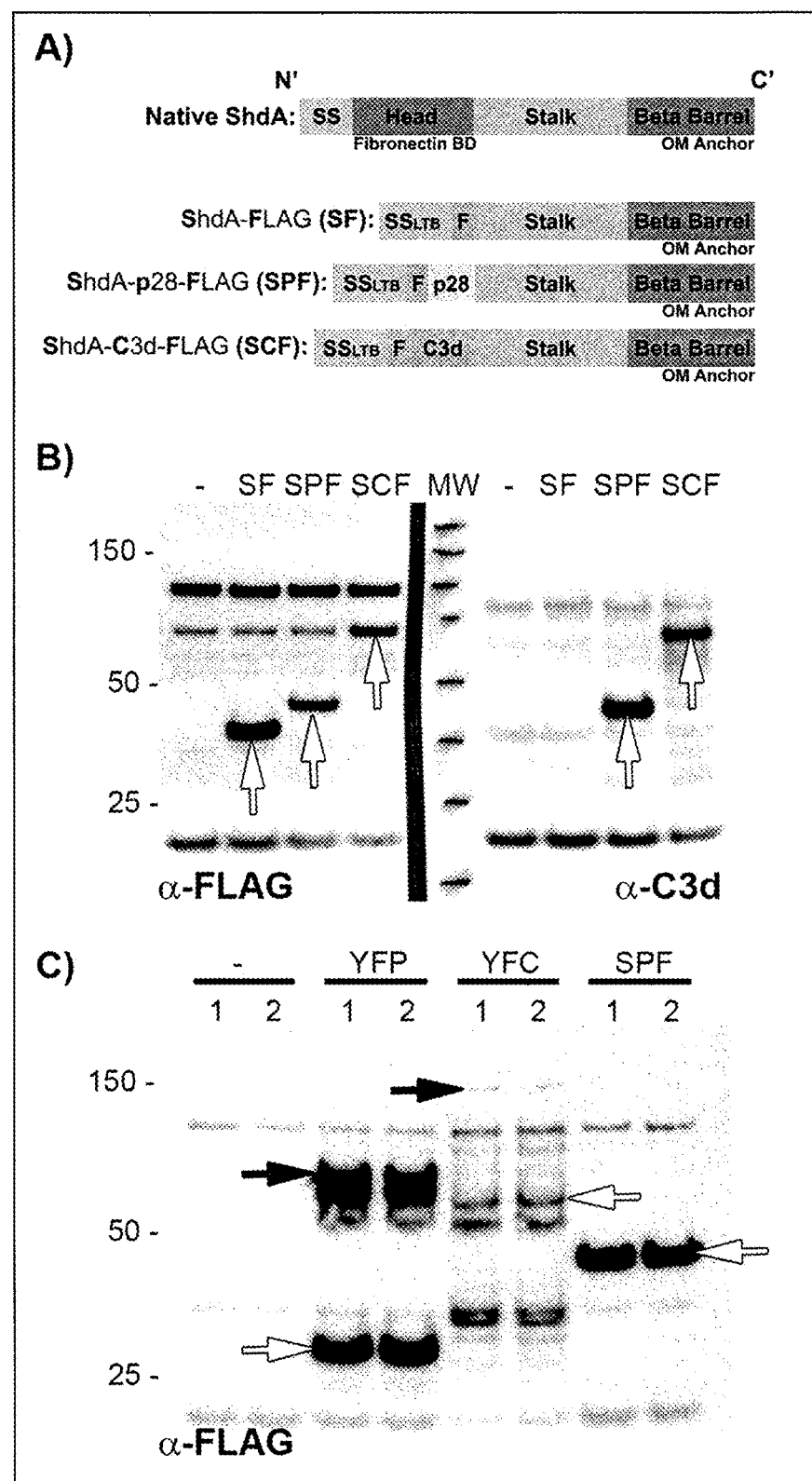

The plasmids pYFC and pYFP express the trimeric YadA-FLAG-C3d/p28 chimeras in *Escherichia coli* (Ec), *Klebsiella pneumoniae* (Kp), and *Francisella tularensis* (Ft) (FIGS. 2B and 2C) and *Shigella flexneri* (FIG. 3C). As anticipated, the FLAG and C3d moieties are exposed at the bacterial surface and are able to bind extra-cellular specific IgG, as seen in FIG. 2D. The plasmids pSPF and pSCF express the monomeric ShdA-FLAG-C3d/p28 chimeras in Ec (FIG. 3B), Ft (not shown) and *Shigella flexneri* (FIG. 3C). In the construction of the plasmids, the native head domains of YadA and ShdA that mediate collagen/fibronectin-binding (see FIGS. 2A and 3A) were removed such that bacteria bearing the plasmids do not bind these extra-cellular, matrix proteins (data not shown).

Figure 4:
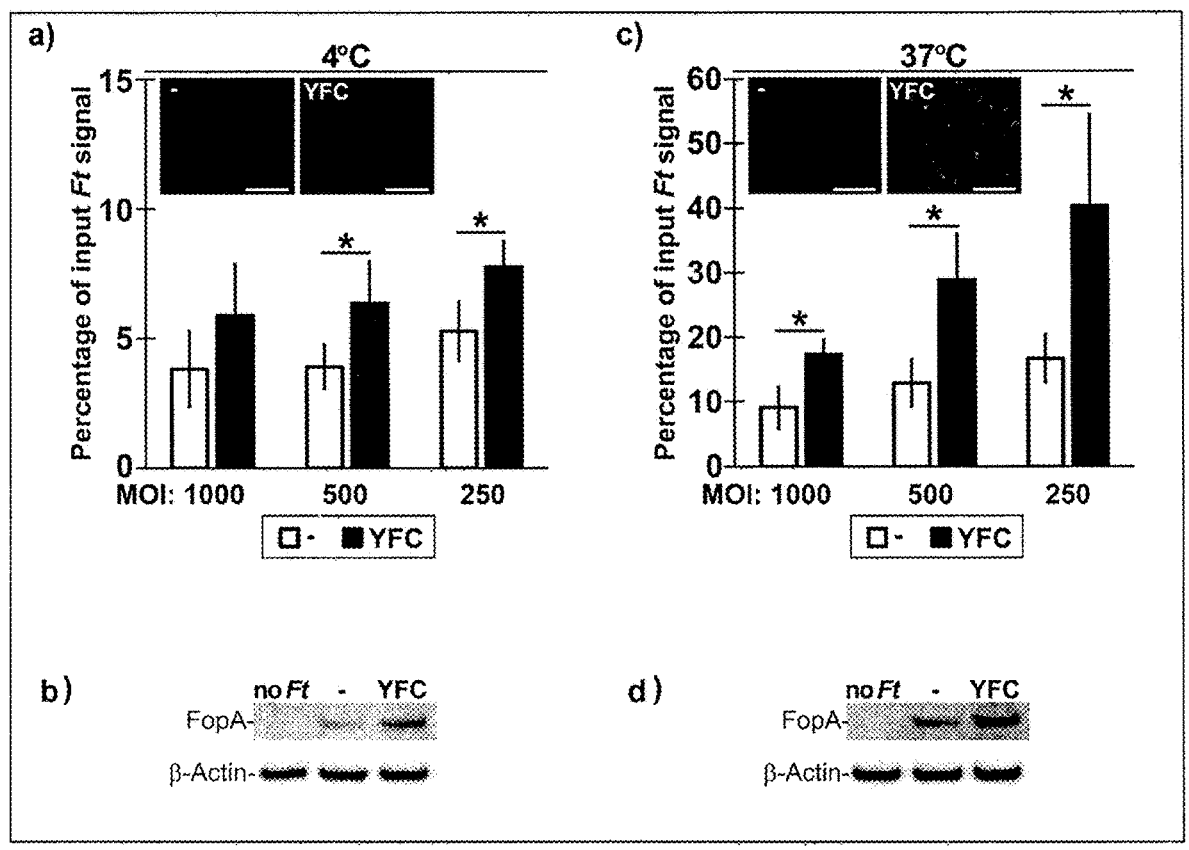
Figure 5:
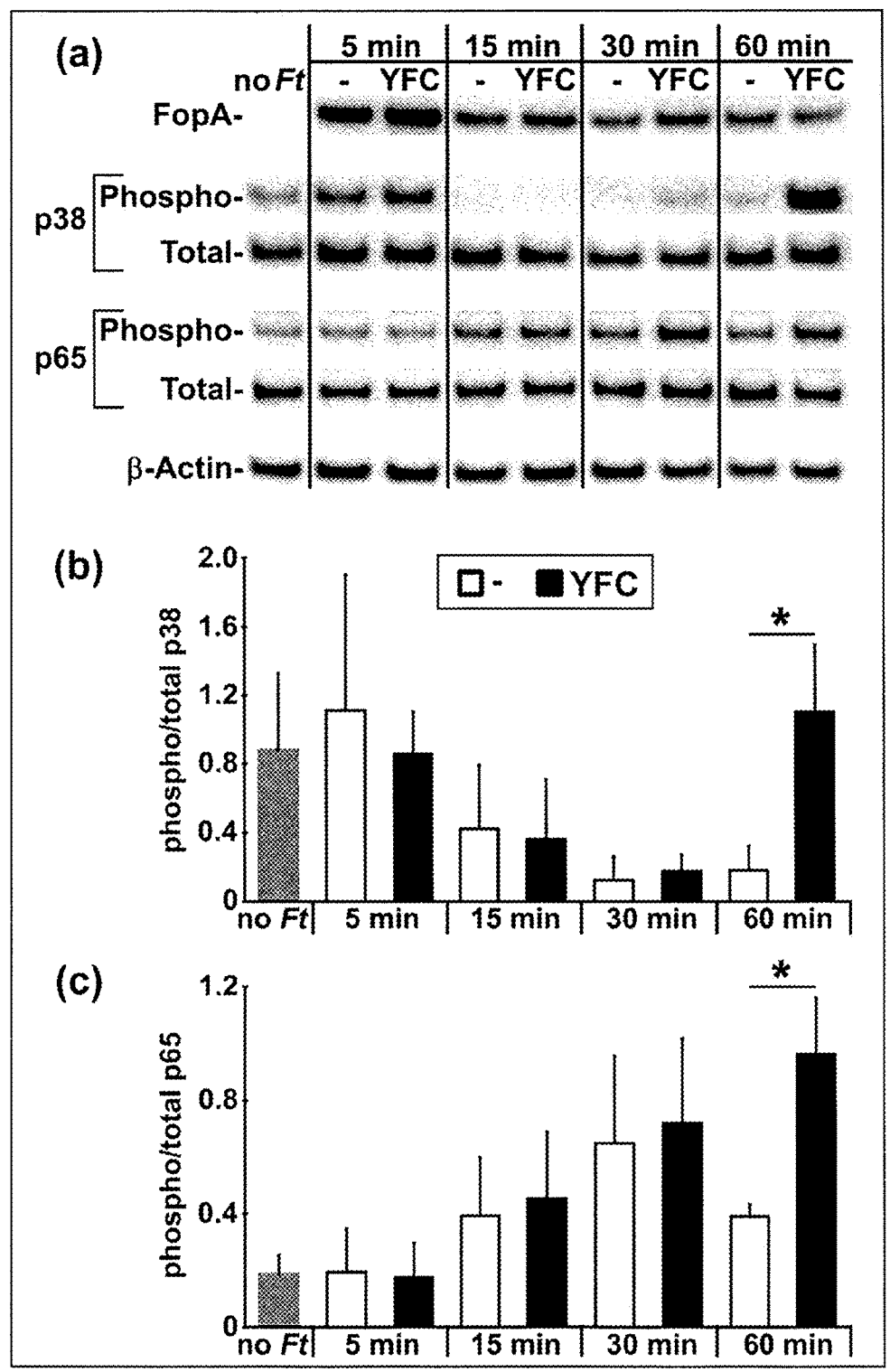

The cellular and immunological mechanisms contributing to vaccinogenic potentiation by YFC was also determined. In cell-based assays, Ft LVS (pF or pYFC) were fluorescently labeled to measure bacterial association with cultured cells. The bacteria-cell incubations were conducted at 4° C. or 37° C. at various MOIs. As seen in FIG. 4, both microscopy and quantitative flourometry revealed that Ft-YFC bound and entered RAW cells at significantly higher levels than Ft-pF. Additional cell-binding experiments with unstained Ft were analyzed by western blot for the bacterial and cellular proteins FopA and β-actin (FIG. 4*b, d*). These results further confirmed the notion that the C3d moiety in YFC functions to enhance binding and apparent phagocytosis. These results were unanticipated as RAW cells are known to express CR3 (the primary receptor for iC3b—not C3d). The expression level of CR2 (the primary receptor for C3d) by RAW cells is less well documented. The results are most readily explained by binding of C3d by CR3. To probe the bacterium-cell interaction promoted by YFC, cellular signaling invoked following interaction with Ft-pF or Ft-pYFC was investigated. Following 30 and 60 minutes of incubation with Ft, RAW cells exposed to Ft-YFC displayed higher levels of phosphorylated p38 and p65 compared to the Ft-pF cells, as shown in FIG. 5.

Figure 6:
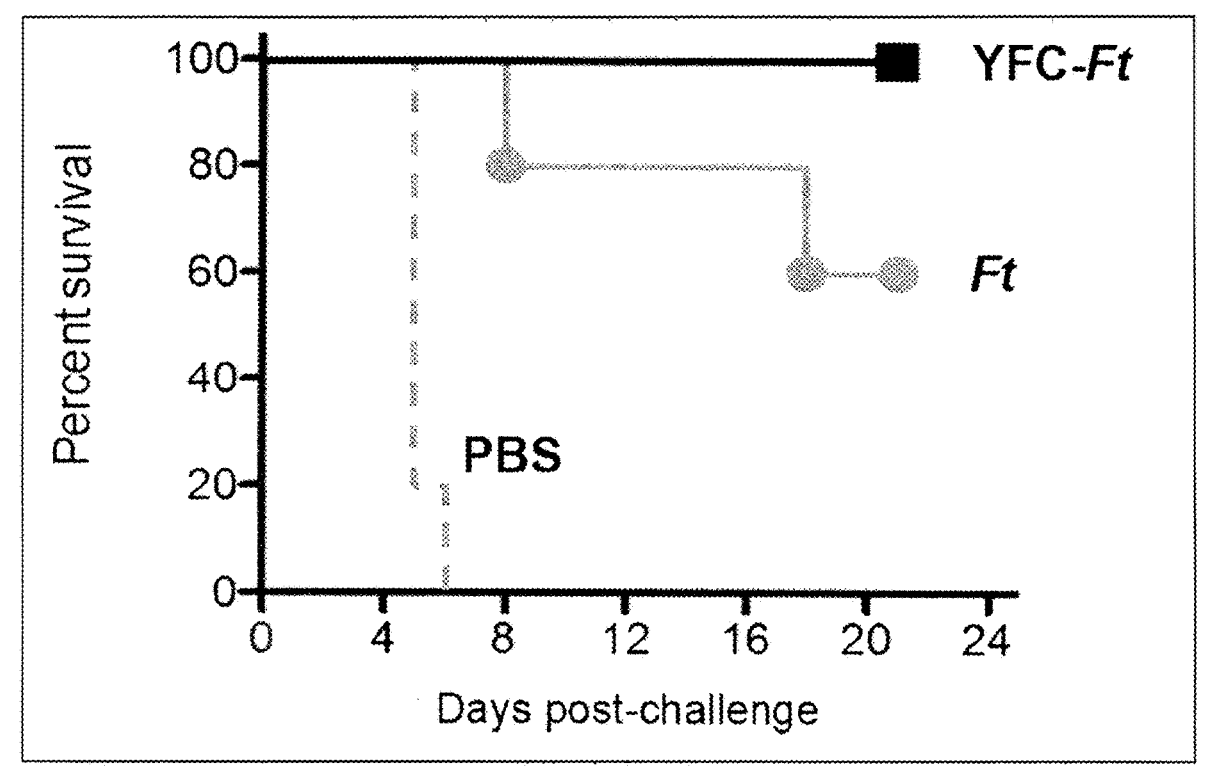

To test the notion that AT-mediated, surface-display of CR-ligands can improve vaccine efficacy, BALB/c mice were immunized with low doses of live Ft LVS harboring either the empty plasmid (pF) or the plasmid (pYFC) of the present invention. As expected for these mice, immunization with Ft provided moderate (~60%) protection against a high-dose Ft LVS challenge, as seen in FIG. 6. In contrast, vaccination with Ft-YFC provided total (100%) protection.

Figure 7A:
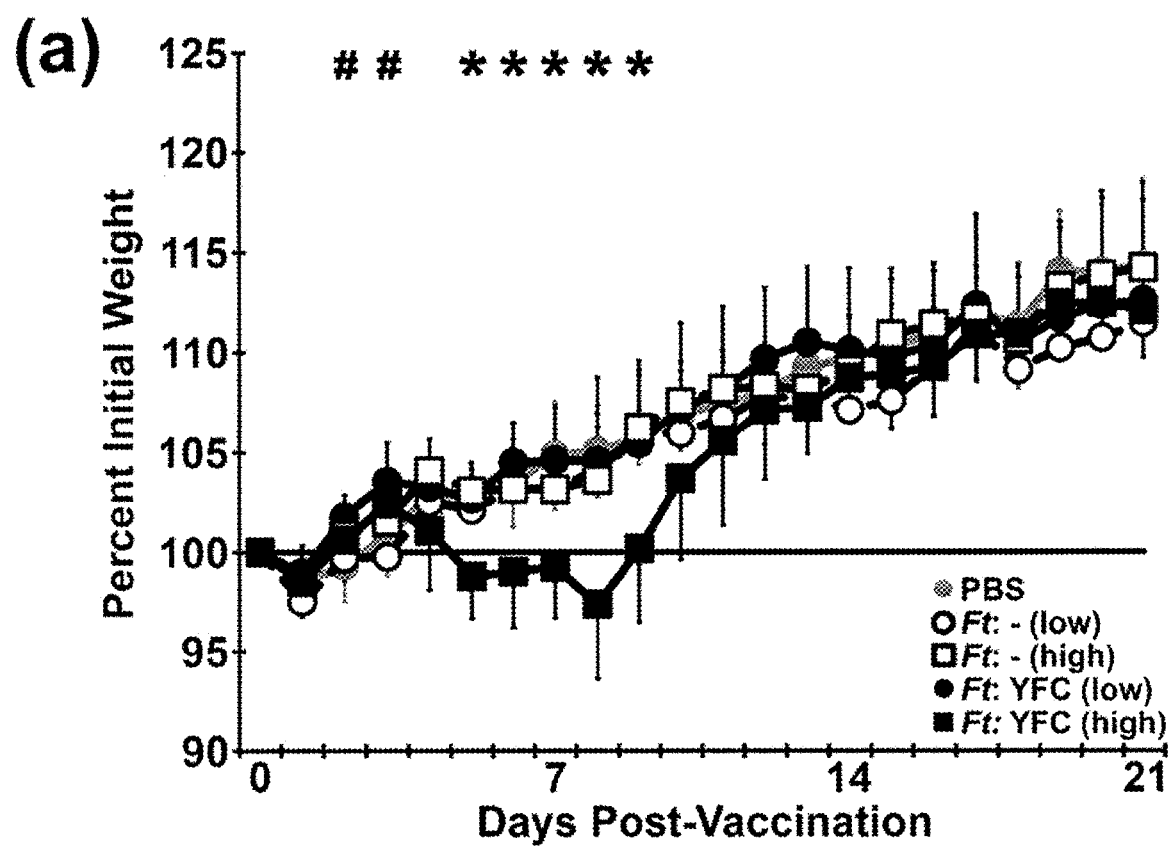
Figure 7B:
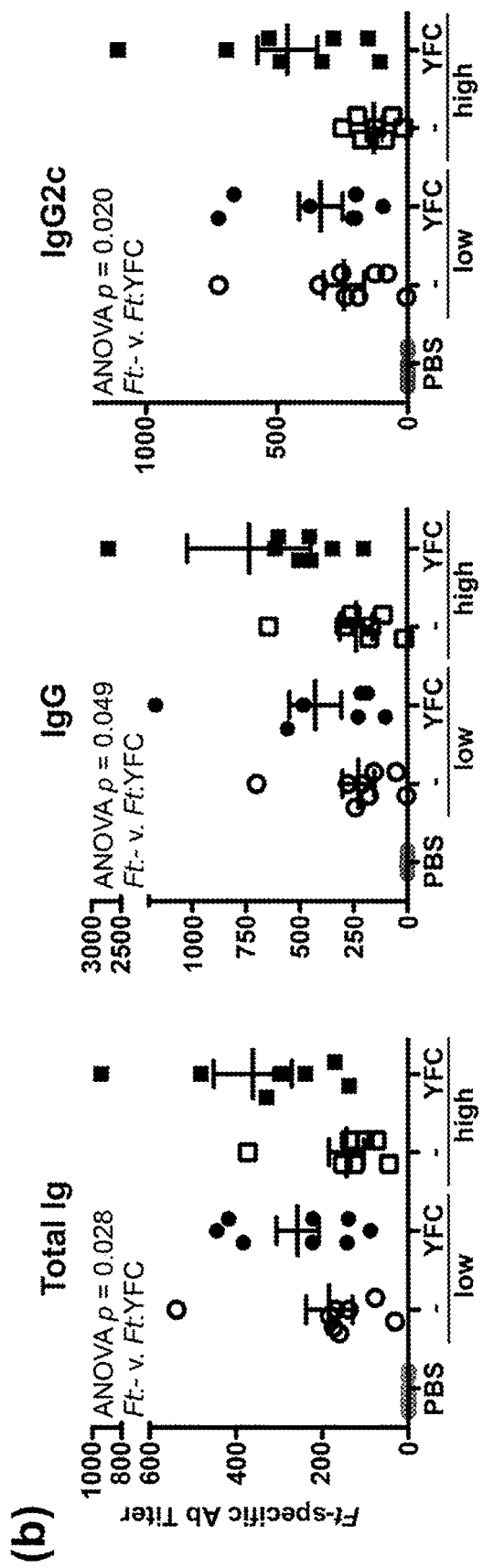

The induction of bacteria-specific antibody following vaccination was examined with graded doses of Ft-pF and Ft-YFC. C57BL/6 mice (n=8; 4M, 4F) were vaccinated intranasally once on day 0 with either a low (~50 CFU) or high (~200 CFU) dose of live Ft LVS bearing pF or pYFC. Daily weight measurements indicate that the higher dose of Ft-YFC tempered normal weight gain for ~5 days after which these mice returned to normal weight (FIG. 7A). Sera drawn on day 21 from vaccinated mice, along with PBS (sham) vaccinated controls, were analyzed by ELISA for Ft-specific titers of total Ig, IgG, and IgG2c. Data were analyzed by both 2-way ANOVA and T-test. As seen in FIG. 7B, mice immunized with Ft-YFC had significantly higher levels of total specific Ab, IgG, and IgG2c. Levels of IgM, IgA, and IgG1 did not differ significantly between Ft-pF and Ft-pYFC immunized mice.

Figure 8A:
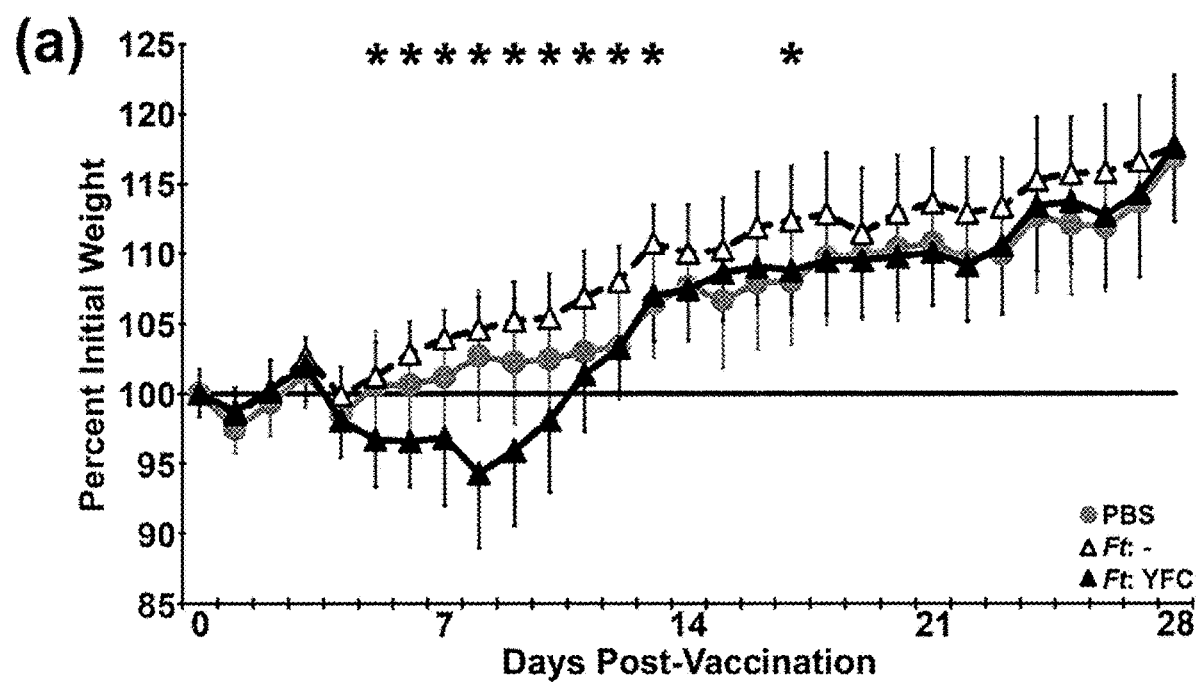
Figure 8B:
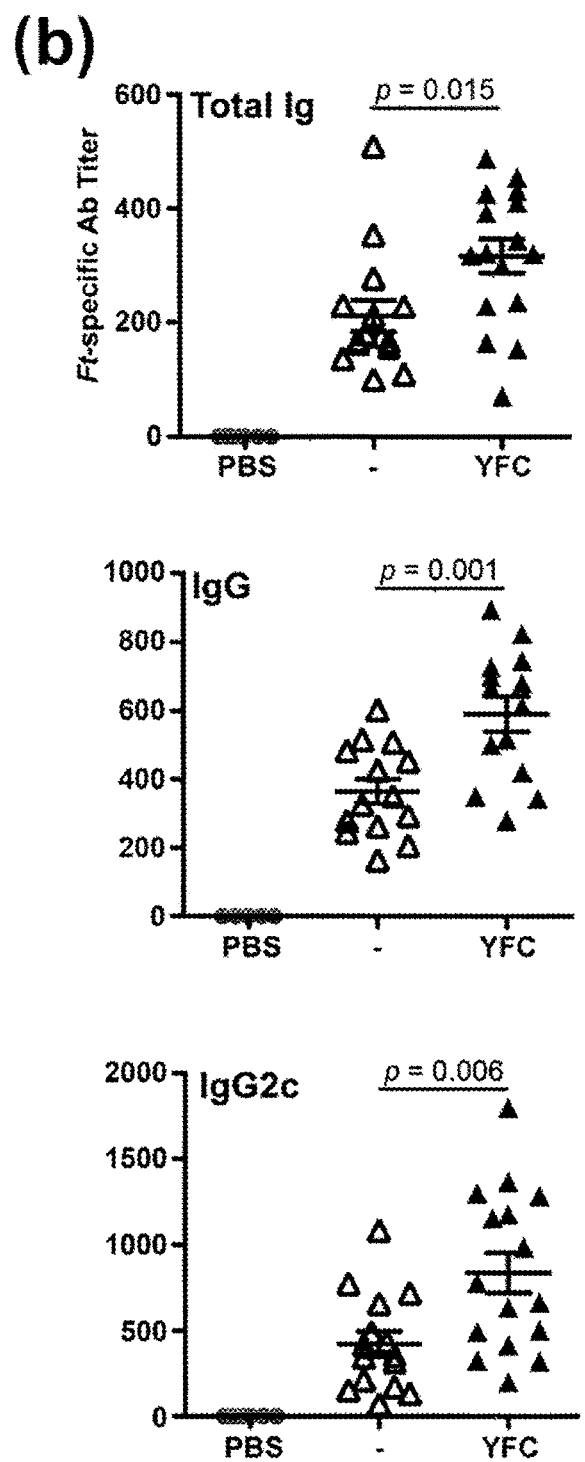
Figures 8C, 8D, 8E:
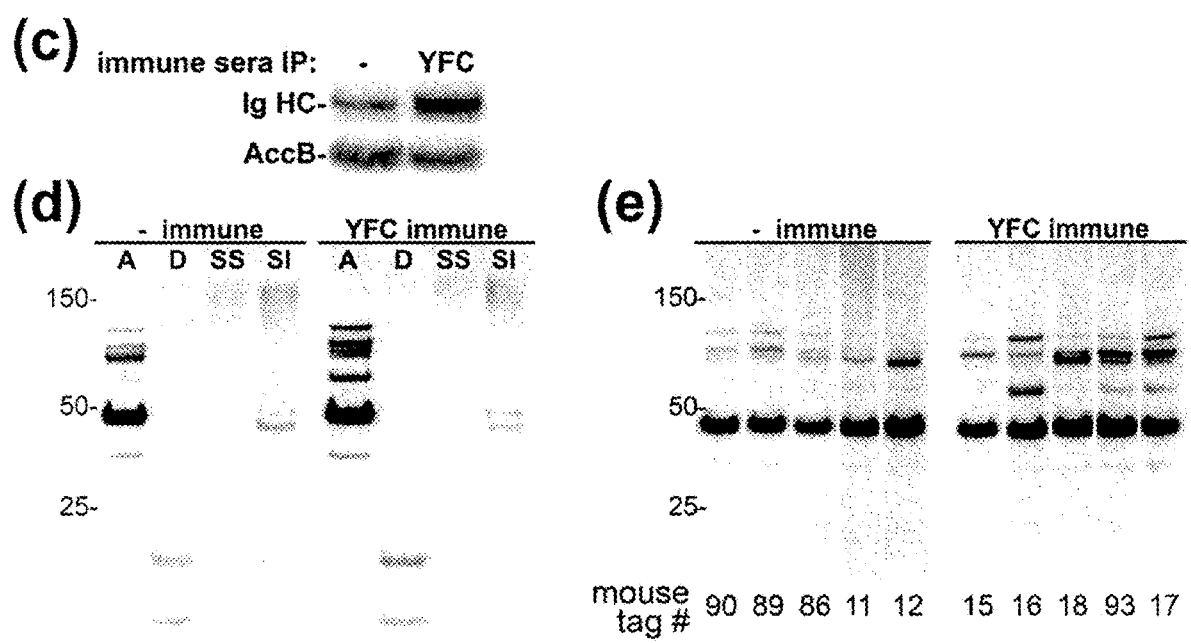
Figure 8F:
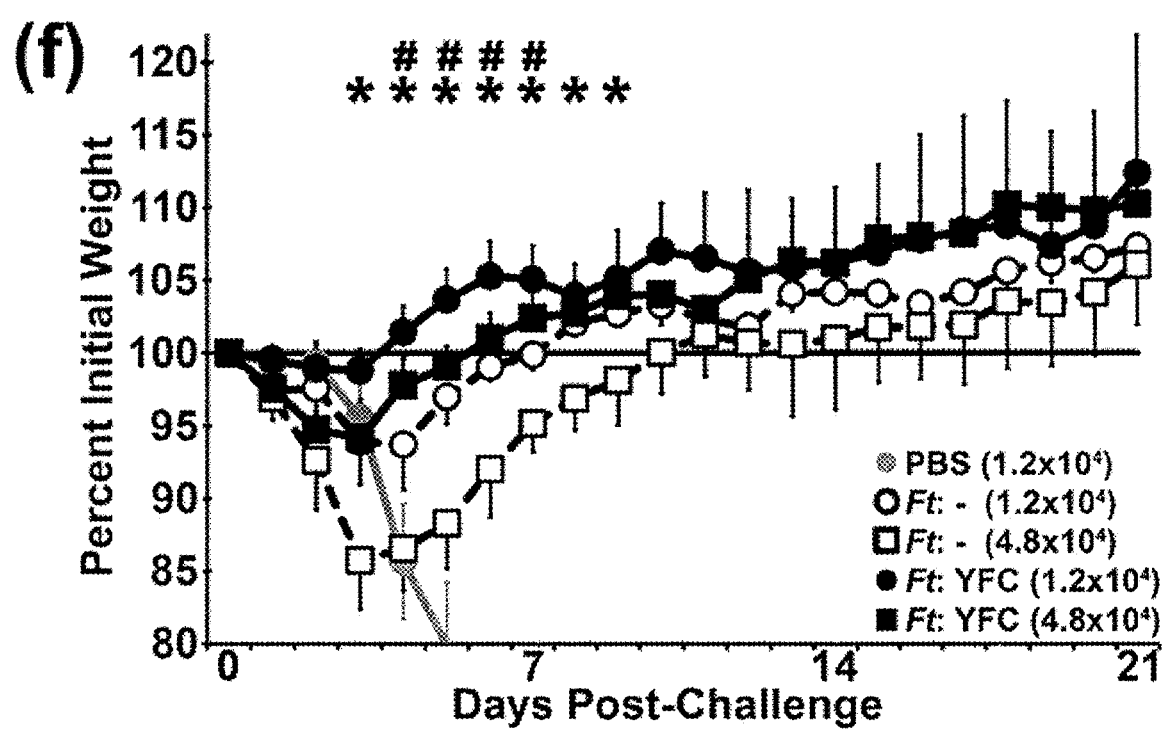
Figure 8G:
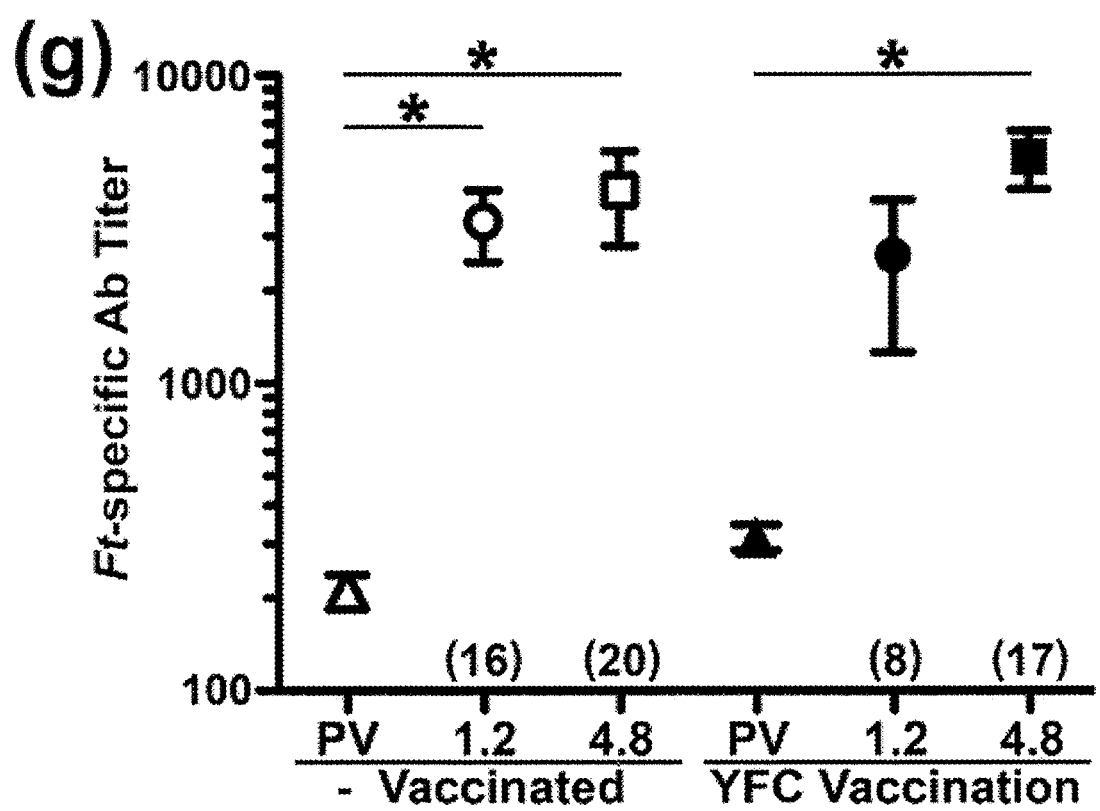

Mice were vaccinated i.n. with a single dose (~200 CFU) of Ft:– and Ft:YFC to further characterize vaccine-induced responses. Among Ft:YFC immunized mice, we again observed a slight decrease in weight following vaccination (FIG. 8a) and significant increases in Ft-specific serum Ig, IgG, and IgG2c titers (FIG. 8b). To determine if the Ft:YFC-induced sera also contained more opsonizing Ab, we used live wildtype Ft to immunoprecipitate serum Ab and detected bound Ig heavy chain by western blot. As shown in FIG. 8c, sera derived from Ft:YFC vaccinated mice contains more bacterial surface-binding Ab than does sera from control immunized mice. These sera pools were also used to probe fractionated Ft (aqueous [A], detergent [D], sarkosyl soluble [SS], sarkosyl insoluble [SI] phases) via western blot to gauge the repertoire of bacterial Ags recognized. For these assays, blots were probed with equal titers of the two sera and, as expected, the majority of bacterial Ags were equivalently recognized (FIG. 8d). However, a small sub-set (~3-4) of A-phase proteins between ~50-100 kDa were more robustly recognized by the Ft:YFC immune sera. When sera from individual animals were similarly used at equal titer, elevated reactivity among Ft:YFC-immunized mice was again observed for these 3-4 A-phase Ags (FIG. 8e). Collectively, Ft:YFC immunized mice produce higher titers of serum Ab that contains more opsonizing Ig and recognizes a broader repertoire of bacterial Ags. Next, these mice were challenged i.n. with one of two doses (12 k or 48 k CFU) of wildtype Ft LVS. These doses were known to be lethal for naïve controls ($LD_{50}$=1,250 CFU) but expected to be sub-lethal for LVS immunized mice. Indeed, PBS controls succumb to challenge by day 9 and all immunized mice ultimately survived. However, differences were apparent in the magnitude and duration of challenge-induced morbidity—as indicated by weight loss. At both challenge doses, Ft:YFC immunized mice lost less weight than their Ft:– counterparts and the differences remained significant for 4-7 days (FIG. 8f). When the days below baseline weight were calculated, these were also significantly lower for Ft:YFC immunized mice. Among the 12 k CFU challenge animals, Ft:YFC immunized mice were below baseline weight for 2.3+/–1.5 d following challenge compared to 6.2+/–0.8 d for the Ft:– vaccinated group (p=0.001). For the 48 k challenge recipients, the corresponding numbers were 5.0+/–0.8 d for the Ft:YFC vaccinated mice and 13.8+/–5.1 d for the control Ft:– mice (p=0.01). Finally, post-vaccination (PV) and post-challenge (PC) serum Ab titers were compared among these groups and made an unexpected observation. Ft:YFC vaccinated mice, which had higher PV titers and less challenge-induced morbidity, appeared to have a muted Ab response to challenge. For Ft:– immunized mice we observed 16 and 20 fold increases (PC/PV) in mean serum Ig titers for the 12 k and 48 k doses respectively (FIG. 8g). For Ft:YFC immunized mice, the fold changes were 8 and 17.

Figure 9:
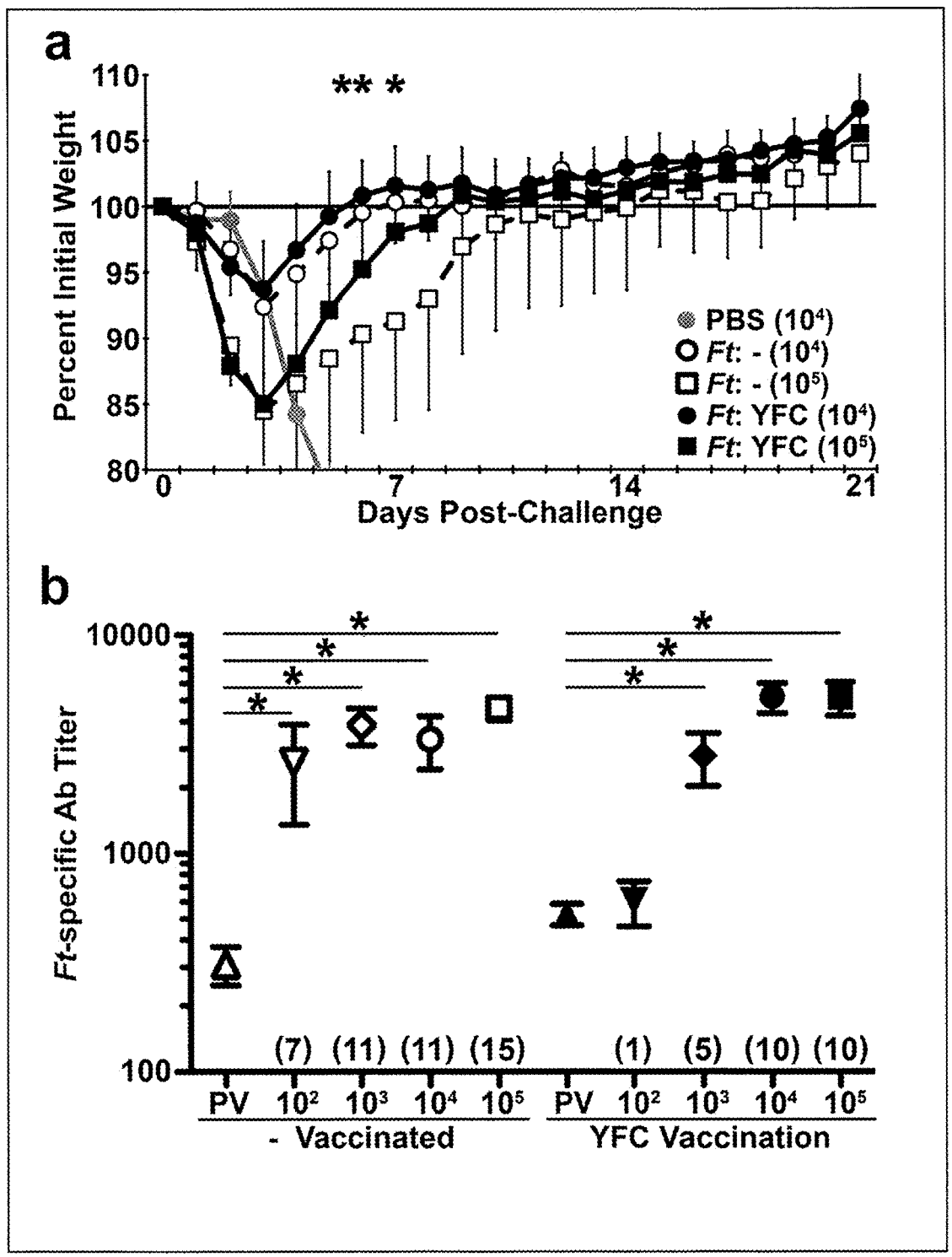

In the preceding works, one isolate of Ft LVS was the basis of the vaccine strains and the challenge agent. As virulence can vary among isolates, we sought to determine if our Ft:YFC strain could similarly protect against challenge with Rocky Mountain Laboratory (RML) Ft LVS which is ~50× more virulent than ATCC LVS. We immunized four groups of mice with our Ft:– or Ft:YFC vaccine strains. The Ft:YFC immunized mice again displayed transient weight loss following vaccination (not shown) and significantly increased serum Ab titers PV (not shown). Vaccinated mice were then challenged i.n. with $10^2$, $10^3$, $10^4$, or $10^5$ CFU of RML Ft LVS. PBS control mice were challenged i.n. with $10^2$, $10^3$, or $10^4$ CFU of RML Ft LVS. Survival among PBS controls was 100%, 37.5%, and 0% respectively; vaccinated mice ultimately survived all challenge doses (not shown). We again noted significant morbidity differences between Ft:– and Ft:YFC immunized mice (FIG. 9a) albeit with some distinctions. In contrast to the homologous challenge results, here the magnitude of peak weight loss did not differ between Ft:– and Ft:YFC immunized mice. However, the latter did recover weight more quickly (FIG. 9a) to yield a trend towards fewer days underweight. Among the $10^5$ CFU challenge animals Ft:YFC immunized mice were below baseline weight for 8.8+/–2.9 d after challenge compared to 12.6+/–6.0 d for the Ft:– vaccinated group (p=0.13). Last, we compared PV and PC serum Ab titers and again observed that mice immunized with Ft:YFC required much higher challenge doses to provoke a significant Ab-recall response (FIG. 9b).

Based on the plasmid design, the plasmids should be applicable beyond Ft. The expression cassettes are driven by a moderately-strong $\sigma^{70}$ promoter, have a canonical N-terminal signal peptide and SPase-I site, and reside on a shuttle vector that replicates in a range of γ-proteobacteria. This class of bacteria includes many notable human pathogens such as *Escherichia*, *Salmonella*, *Shigella*, *Yersinia* and *Klebsiella* on one end of this spectrum, with *Haemophilus*, *Vibrio*, and *Pseudomonas* in the middle, followed by the more distally related *Francisella*, *Legionella* and *Coxiella* on the other end. As all of these bacteria are gram-negative and have autotransporters, the plasmids of the present invention should function in many of the γ-proteobacteria. Indeed, the plasmids, with no modifications, were readily transformed into *Escherichia*, *Shigella*, *Klebsiella*, and *Francisella*. The resulting strains express the FLAG- and C3d-positive fusions (FIGS. 2 and 3) and have surface-exposed FLAG and C3 moieties.

Thus, the six plasmids of the present invention, pYF, pYFC, pYFP, pSF, pSPF, and pSCF are rapidly applicable to a broad range of the γ-proteobacteria; pYFC and pYFP yield surface-exposed CR ligands. In the context of Ft, bacteria harboring plasmids according to the present invention have increased association with CR-expressing immune cells, see FIG. 4, and provoke heightened signaling responses, see FIG. 5. When administered to animals as a vaccine, bacteria modified according to the present invention elicit more specific antibodies, see FIGS. 7 and 8, and better survive lethal challenges, see FIGS. 6, 8, and 9.

EXAMPLE

Fragments of yadA were PCR amplified from *Yersina enterolitica* genomic DNA and cloned into pCR 2.1 TOPO prior to DNA sequence analysis. The first fragment, encoding the YadA signal sequence (YadA SS), was amplified using primers Ye YadA 5'Eco (GAA TTC ACT AAA GAA ATA TAA AAG GTG CTT ACA) (SEQ ID NO: 4) and 3' YadA SS_SacI (GAG CTC GTC ATT ATT GGC AAA TGC) (SEQ ID NO: 5) containing engineered EcoRI and SacI restriction sites. The second fragment, encoding the YadA stalk and β-barrel (YadA SβB), was amplified using primers 5' SacI_FLAG_YadA cterm (GAG CTC GAC TAT AAG GAC GAT GAT GAC AAA TTG GAT ATG GCA AAA AAA CAC TCA AAT AG) (SEQ ID NO: 6) and Ye YadA 3Stop_PmeI (GT TTA AAC CTA TTA CCA CTC GAT ATT AAA TGA TGC ATT) (SEQ ID NO: 7) containing engineered SacI and PmeI restriction sites. 5' SacI_FLAG_YadA encodes an engineered, in-frame FLAG tag; Ye YadA 3Stop_PmeI contains an additional in-frame stop codon. Following digestion of pTOPO:YadA SβB (KH Ec strain #529) with EcoRI and PmeI, YadA fragment 2 was gel-purified and ligated to EcoRI/EcoRV digested pF resulting in plasmid pF:YadSβB (KH Ec strain #531). The first fragment (encoding YadSS) was liberated from pTOPO:YadA SS (KH Ec strain #528) with EcoRI and SacI, gel-purified, and ligated to similarly digested pF:YadSβB.

Referring to FIG. 10, the salient features of the resulting plasmid (pYF, KH Ec strain #533) include an M13R priming site (5' thick underlined), a Ft groEL promoter (italics) driving expression of an open-reading frame (upper case) containing the YadA SS, a SacI site (single underline), a FLAG-tag (double underline) and YadA SβB followed by 2 stop codons (bold) and a reverse priming site for pF-R (CAT ACC TGC CGA ACT GGT CGG; 3'thick underlined)(SEQ ID NO: 8). The SacI site in pYF subsequently served as the recipient site for SacI flanked inserts encoding complement receptor ligands (below).

Referring to FIG. 11, DNA encoding C3d was PCR amplified from plasmid KH Ec #305, a cloning intermediate) using 5' C3d w/linker AgeI (ACC GGT GGG GGG GAA CAG AAC ATG ATT GGC ATG) (SEQ ID NO: 9) and 3' C3d w/linker XmaI_SalI (GTC GAC GGA CCC GGG ACC TCC GTT CAA GTC CTT ATG GTC) (SEQ ID NO: 10) and cloned into pCR Topo2.1 prior to DNA sequence analysis. The resulting plasmid, KH Ec #489, was subject to site directed mutagenesis with 5' Mut. Destroy SacI in C3d (G CAA GAG GCC CTG GAG CTG ATC AAG AAA GGG TAC) (SEQ ID NO: 11) and 3' Mut. Destroy SacI in C3d (GTA CCC TTT CTT GAT CAG CTC CAG GGC CTC TTG C) (SEQ ID NO: 12) to eliminate the C3d-internal SacI site. The resulting mutated C3d DNA (C3dΔSacI) was PCR amplified with 5' SacI_C3d (GAG CTC GGG GGG GAA CAG AAC ATG ATT GG) (SEQ ID NO: 13) and 3' C3d_SacI (GAG CTC ACC TCC GTT CAA GTC CTT ATG GTC) (SEQ ID NO: 14) and cloned into pCR 2.1 Topo yielding pTOPO:C3dΔSacI (KH Ec strain #532). Following digestion with SacI, the C3dΔSacI fragment was gel-purified and ligated to SacI digested pYF (above). A clone with the C3d fragment (highlighted in light grey and underlined with dashes in FIG. 11) in the same orientation as YadA was identified and termed pYFC (KH Ec strain #536).

Referring to FIG. 12, DNA encoding murine p28, flanked by SacI sites, was generated via synthetic overlap PCR using primers P28 FWD SacI (for YadA) (TTG GAG CTC AAG TTT CTG AAC ACA GCC AAA GAT CGG AAC CGC TGG GAG GAG CCT GAC CAG CAG CTC TAC AAC GTA GAG GC) (SEQ ID NO: 15) and P28 RVS SacI (for YadA) (TCC GAG CTC GCT GCT GCT GCC ACC TCC TCC GCT GCT CCC ACC TCC CCC GGC GTA GGA TGT GGC CTC TAC GTT GTA GAG CTG CTG) (SEQ ID NO: 16) and was cloned into pCR Topo2.1 yielding TOPO:SacI-p28-SacI (KH Ec strain #665). pTOPO:SacI-p28-SacI was digested with SacI then the p28 fragment was gel purified and ligated to SacI-digested pYF (above). A clone with the p28 fragment in the same orientation as YadA was identified via DNA sequencing and was termed pYFP (KH Ec strain #674). In FIG. 12, the p28-encoding region is highlighted in light grey and underlined with dashes.

Referring to FIG. 13, for pSF, the truncated stalk and complete (β-barrel of ShdA was PCR amplified from Salmonella enterica typhimurium genomic DNA using primers ShdA FWD EcoRI NheI (GAA TTC GGA GCT AGC CCG CAG TAC CGT GCG GAT ATC)(SEQ ID NO: 20) and ShdA-FLAG RVS BamHI (GCT AAG GGA TCC AGT TAT AGC GCA GAT TGA GGC TAC)(SEQ ID NO: 21) and was cloned into pCR Topo2.1 yielding TOPO:ShdA-SβB (KH Ec Strain #548). Following digestion with EcoRI and BamHI, the ShdA-SβB fragment was ligated to pF that had also been cut with EcoRI and BamHI, yielding pF: ShdA-SβB (KH Ec Strain #564). DNA encoding the LTB (Ec heat-labile enterotoxin B) signal sequence and a FLAG tag was generated by synthetic overlap PCR using LTBss FWD XbaI (for FLAG tagged) (TCT AGA ATG AAT AAA GTA AAA TTT TAT GTT TTA TTT ACG GCG TTA CTA TCC TCT CTA TGT GC)(SEQ ID NO: 22) containing an XbaI site and LTBss RVS FLAG EcoRI (GAA TTC TTT GTC ATC ATC GTC CTT ATA GTC TCT AGC TCC GTG TGC ACA TAG AGA GGA TAG TAA CGC CG)(SEQ ID NO: 23) containing an EcoRI site. The resulting fragment was cloned into pCR Topo2.1 yielding TOPO:LTBss-FLAG (KH Ec strain #552). Following digestion with EcoRI, the LTBss-FLAG segment was gel purified and ligated to pF:ShdA-SβB that was also cut with EcoRI, colonies were screened for insert in the correct direction, yielding pF:LTBss-FLAG-ShdA-SβB (KH Ec strain #574). We next mutated the EcoRI site that is upstream of LTBss-FLAG in order to allow for utilization of the downstream EcoRI/NheI insertion sites. Site directed mutagenesis was performed with 5 mutagen remove EcoRI monomer (GCA GGT ACC ATA TGT TTT CGC CCT TTC TAG)(SEQ ID NO: 24) and 3 mutagen remove EcoRI monomer (CTA GAA AGG GCG AAA ACA TAT GGT ACC TGC) (SEQ ID NO: 25) using the Agilent QuickChange Site-Directed Mutagenesis kit. Mutation was confirmed, and the resulting plasmid was termed pSF (KHEc strain #609) (SEQ ID NO:17, FIG. 13).

Referring to FIG. 14, for pSPF the murine p28 segment was generated via synthetic overlap PCR using primers P28 FWD EcoRI (for ShdA) (TTG GAA TTC AAG TTT CTG AAC ACA GCC AAA GAT CGG AAC CGC TGG GAG GAG CCT GAC CAG CAG CTC TAC AAC GTA GAG GC)(SEQ ID NO: 26) and P28 RVS NheI (for ShdA) (TCC GCT AGC GCT GCT GCC ACC TCC TCC GCT GCT CCC ACC TCC CCC GGC GTA GGA TGT GGC CTC TAC GTT GTA GAG CTG CTG)(SEQ ID NO: 27) and was cloned into pCR Topo2.1 yielding TOPO:EcoRI-p28-NheI (KH Ec strain #649). TOPO:EcoRI-p28-NheI was digested with EcoRI and NheI; the resulting p28 segment was ligated into EcoRI- and NheI-digested pSF to generate the pSPF plasmid (KH Ec strain #656) (SEQ ID NO:18, FIG. 14).

Referring to FIG. 15, for pSCF the DNA encoding C3d was PCR amplified from plasmid TOPO:C3dASacI (KH Ec strain #532) using primers 5' EcoRI C3d for monomers (GAA TTC GGG GGG GAA CAG AAC ATG ATT GGC ATG)(SEQ ID NO: 28) and 3' NheI_C3d for monomers (GCT AGC ACC TCC GTT CAA GTC CTT ATG GTC) (SEQ ID NO: 29) and was cloned into pCR Topo2.1 yielding TOPO:EcoRI-C3dASacI-NheI (KH Ec strain #607). TOPO:

EcoRI-C3dASacI-NheI was digested with EcoRI and NheI; the resulting C3d segment was ligated into EcoRI- and NheI-digested pSF to generate the pSCF plasmid (KH Ec strain #618) (SEQ ID NO:19, FIG. 14).

The pSF, pSPF, and pSCF-related primers are as follows: ShdA FWD EcoRI NheI-GAA TTC GGA GCT AGC CCG CAG TAC CGT GCG GAT ATC (SEQ ID NO: 20); ShdA-FLAG RVS BamHI—GCT AAG GGA TCC AGT TAT AGC GCA GAT TGA GGC TAC (SEQ ID NO: 21); LTBss FWD XbaI (for FLAG tagged)—TCT AGA ATG AAT AAA GTA AAA TTT TAT GTT TTA TTT ACG CGG TTA CTA TCC TCT CTA TGT GC (SEQ ID NO: 22); LTBss RVS FLAG EcoRI-GAA TTC TTT GTC ATC ATC GTC CTT ATA GTC TCT AGC TCC GTG TGC ACA TAG AGA GGA TAG TAA CGC CG (SEQ ID NO: 23); 5 mutagen remove EcoRI monomer—GCA GGT ACC ATA TGT TTT CGC CCT TTC TAG (SEQ ID NO: 24); 3 mutagen remove EcoRI monomer—CTA GAA AGG GCG AAA ACA TAT GGT ACC TGC (SEQ ID NO: 25); P28 FWD EcoRI (for ShdA)—TTG GAA TTC AAG TTT CTG AAC ACA GCC AAA GAT CGG AAC CGC TGG GAG GAG CCT GAC CAG CAG CTC TAC AAC GTA GAG GC (SEQ ID NO: 26); P28 RVS NheI (for ShdA)- TCC GCT AGC GCT GCT GCC ACC TCC TCC GCT GCT CCC ACC TCC CCC GGC GTA GGA TGT GGC CTC TAC GTT GTA GAG CTG CTG (SEQ ID NO: 27); 5' EcoRI_C3d for monomers—GAA TTC GGG GGG GAA CAG AAC ATG ATT GGC ATG (SEQ ID NO: 28); 3' NheI_C3d for monomers—GCT AGC ACC TCC GTT CAA GTC CTT ATG GTC. (SEQ ID NO: 29).

What is claimed is:

1. A platform for improving the immunologic response of a bacterial vaccine, comprising a plasmid having a first nucleic acid region that encodes a cleavable, N-terminal signal sequence (SS), a second nucleic acid region encoding at least a portion of a ligand for complement receptor two (CR2) or three (CR3), a third nucleic acid region encoding a protein tag, and a fourth nucleic acid sequence encoding a C-terminal, (β-barrel OM-insertion domain of an autotransporter, wherein the plasmid has a sequence selected from group consisting of SEQ ID NO: 1, SEQ ID NO: 2, SEQ ID NO: 3, SEQ ID NO: 17, SEQ ID NO: 18, and SEQ ID NO: 19.

2. The platform of claim 1, wherein the autotransporter is selected from the group consisting of a trimeric *Yersinia* adhesion protein A (YadA) and a monomeric *Salmonella* adhesion protein A (ShdA).

3. The platform of claim 1, wherein the ligand comprises complement component C3d.

4. The platform of claim 1, wherein the ligand comprises complement receptor-binding peptide p28.

5. The platform of claim 1, wherein the protein tag comprises a FLAG tag.

6. A bacteria containing a plasmid having a first nucleic acid region that encodes a cleavable, N-terminal signal sequence (SS), a second nucleic acid region encoding at least a portion of a ligand for complement receptor two (CR2) or three (CR3), a third nucleic acid region encoding a protein tag, and a fourth nucleic acid sequence encoding a C-terminal, β-barrel OM-insertion domain of an autotransporter, wherein the plasmid has a sequence selected from group consisting of SEQ ID NO: 1, SEQ ID NO: 2, SEQ ID NO: 3, SEQ ID NO: 17, SEQ ID NO: 18, and SEQ ID NO: 19.

7. The bacteria of claim 6, wherein the autotransporter is selected from the group consisting of a trimeric *Yersinia* adhesion protein A (YadA) and a monomeric *Salmonella* adhesion protein A (ShdA).

8. The bacteria of claim 6, wherein the ligand comprises complement component C3d.

9. The bacteria of claim 6, wherein the ligand comprises complement receptor-binding peptide p28.

10. A method of improving the immunologic response of a bacterial vaccine, comprising the steps of:

obtaining an amount of bacteria for use as a bacterial vaccine; and transforming the amount of bacteria with a plasmid having a first nucleic acid region that encodes a cleavable, N-terminal signal sequence (SS), a second nucleic acid region encoding at least a portion of a ligand for complement receptor two (CR2) or three (CR3), a third nucleic acid region encoding a protein tag, and a fourth nucleic acid sequence encoding a C-terminal, β-barrel OM-insertion domain of an autotransporter, wherein the plasmid has a sequence selected from group consisting of SEQ ID NO: 1, SEQ ID NO: 2, SEQ ID NO: 3, SEQ ID NO: 17, SEQ ID NO: 18, and SEQ ID NO: 19.

11. The method of claim 10, wherein the autotransporter is selected from the group consisting of a trimeric *Yersinia* adhesion protein A (YadA) and a monomeric *Salmonella* adhesion protein A (ShdA).

12. The method of claim 10, wherein the ligand comprises complement component C3d.

13. The method of claim 10, wherein the ligand comprises complement receptor-binding peptide p28.

* * * * *